United States Patent
Rebatchouk et al.

(10) Patent No.: US 9,161,894 B2
(45) Date of Patent: Oct. 20, 2015

(54) USE OF N-(4-METHOXYPHENYL)-1-PHENYL-1H-PYRAZOL-3-AMINE AND RELATED COMPOUNDS

(75) Inventors: Dmitri Rebatchouk, Flemington, NJ (US); Felix Sheinerman, New York, NY (US)

(73) Assignee: NPHARMAKON, LLC, Piscataway, NJ (US)

( * ) Notice: Subject to any disclaimer, the term of this patent is extended or adjusted under 35 U.S.C. 154(b) by 0 days.

(21) Appl. No.: 14/001,575

(22) PCT Filed: Mar. 1, 2012

(86) PCT No.: PCT/US2012/027298
§ 371 (c)(1),
(2), (4) Date: Aug. 26, 2013

(87) PCT Pub. No.: WO2012/141815
PCT Pub. Date: Oct. 18, 2012

(65) Prior Publication Data
US 2014/0010773 A1  Jan. 9, 2014

Related U.S. Application Data

(60) Provisional application No. 61/448,080, filed on Mar. 1, 2011.

(51) Int. Cl.
| | |
|---|---|
| *A61K 31/415* | (2006.01) |
| *A61K 8/49* | (2006.01) |
| *A61K 9/00* | (2006.01) |
| *A61K 9/06* | (2006.01) |
| *A61K 47/32* | (2006.01) |

(Continued)

(52) U.S. Cl.
CPC .............. *A61K 8/494* (2013.01); *A61K 8/4946* (2013.01); *A61K 9/0014* (2013.01); *A61K 9/06* (2013.01); *A61K 31/415* (2013.01); *A61K 47/32* (2013.01); *A61Q 19/02* (2013.01); *A61K 47/10* (2013.01); *A61K 2800/782* (2013.01)

(58) Field of Classification Search
None
See application file for complete search history.

(56) References Cited

U.S. PATENT DOCUMENTS

| | | |
|---|---|---|
| 4,810,719 A | 3/1989 | Appleton et al. |
| 5,428,044 A | 6/1995 | Bantick et al. |

(Continued)

FOREIGN PATENT DOCUMENTS

WO    2005115385 A1    12/2005

OTHER PUBLICATIONS

Blackham, et al.(FPL 62065, a topically active 5-lipoxygenase/cycolocygenase inhibitor, Agents Actions, Jun. 1990; 30(3-4):432-42).*

(Continued)

*Primary Examiner* — Robert A Wax
*Assistant Examiner* — Melissa Mercier
(74) *Attorney, Agent, or Firm* — David W. Ladner; Ladner Patent Management LLC (57) ABSTRACT

This invention provides methods for treating diseases or conditions wherein the inhibition of Kit protein kinase may be beneficial, using pharmaceutical or cosmetic compositions comprising N-(4-methoxyphenyl)-1-phenyl-1H-pyrazol-3-amine (FPL-62064) and related compounds. This invention also relates to the treatment of skin disorders, such as hyperpigmentation and cutaneous mastocytosis, and to cosmetic uses such as skin lightening.

3 Claims, 2 Drawing Sheets

Inhibition of Kit biochemical activity by FPL-62064, $IC_{50}$ = 6.9 μM (51) Int. Cl.
  *A61Q 19/02*  (2006.01)
  *A61K 47/10*  (2006.01)

(56) References Cited

U.S. PATENT DOCUMENTS

| | | | |
|---|---|---|---|
| 6,136,839 A * | 10/2000 | Isakson et al. | 514/406 |
| 6,977,159 B1 | 12/2005 | Longley | |
| 7,132,441 B2 | 11/2006 | Gregory et al. | |
| 2006/0193797 A1 | 8/2006 | Zhang et al. | |
| 2009/0220583 A1 | 9/2009 | Pereswetoff-Morath et al. | |

OTHER PUBLICATIONS

Blackman et al. (FPL 62065, a topically active 5-lipoxygenase/cycolocygenase inhibitor, Agents Active, Jun. 1990:30(3-4):432-42.*

Grimes et al. "Light microscopic, immunohistochemical, and ultrastructural alterations in patients with melasma"; Am J Dermatopathol 27:96 (2005).

Juurikivi et al. "Inhibition of c-kit tyrosine kinase by imatinib mesylate induces apoptosis in mast cells in rheumatoid synovia . . . "; Ann Rheum Dis 64:1126 (2005).

Legros et al. "Imatinib mesilate (Glivec): a systemic depigmenting agent for extensive vitiligo?"; Br J Dermatol 153:691(2005).

McPartlin et al. "Loss of skin pigment caused by imatinib therapy" Br J Haematol 129:448 (2005).

Roskoski "Structure and regulation of Kit protein-tyrosine kinase—The stem cell factor receptor"; Biochem Biophys Res Commun 338:1307 (2005).

Biers et al. "The functional effects of a c-kit tyrosine inhibitor onguinea-pig and human detrusor"; BJU Int 97:612 (2006).

Brazzelli et al. "Vitiligo-Like Lesions and Diffuse Lightening of the Skin in a Pediatric Patient Treated with Imatinib Mesylate . . . "; Pediatr Dermatol 23:175 (2006).

Curtin et al. "Somatic Activation of KIT in Distinct Subtypes of Melanoma"; J Clin Oncol 24:4340 (2006).

Faivre et al. "Safety, Pharmacokinetic, and Antitumor Activity of SU11248, a Novel Oral Multitarget Tyrosine Kinase Inhibitor . . . "; J Clin Oncol 24:25(2006).

Gotlib "KIT Mutations in Mastocytosis and Their Potential as Therapeutic Targets"; Immunol Allergy Clin North Am 26:575 (2006).

Kang et al."The dermal stem cell factor and c-kit are overexpressed in melasma"; Br J Dermatol 154:1094 (2006).

Reber et al. "Stem cell factor and its receptor c-Kit as targets for inflammatory diseases"; Eur J Pharmacol 533:327 (2006).

Draelos "Skin lightening preparations and the hydroquinone controversy"; Dermatol Ther 20:308 (2007).

Jasim et al."Treatment of pulsed dye laser-resistant port wine stain birthmarks"; J Am Acad Dermatol 57:677 (2007).

Kubota et al. (2007) Hinyokika Kiyo 53:435 (English Abstract only).

Eklund et al. "Maintained Efficacy of the Tyrosine Kinase Inhibitor Imatinib Mesylate in a Patient With Rheumatoid Arthritis"; J Clin Rheumatol 14:294 (2008).

Watanabe "Basics of laser application to dermatology"; Arch Dermatol Res 300 Suppl 1:S21 (2008).

Campbell et al. "Disappearance of Lentigines in a Patient Receiving Imatinib Treatment for Familial Gastrointestinal Stromal Tumor Syndrome"; Arch Dermatol 145:1313 (2009).

Khanna et al. "Catching Cancer by theTail: New Perspectives on the Use of Kinase Inhibitors"; Clin Cancer Res 15:3645 (2009).

Smalley et al. "c-KIT signaling as the driving oncogenic event in sub-groups of melanomas"; Histol Histopathol 24:643 (2009).

Vernon et al. "Resolution of Rheumatoid Arthritis Symptoms With Imatinib Mesylate"; J Clin Rheumatol 15:267 (2009).

Zhao et al. "Efficacy and prognosis of chronic myeloid leukemia treated with imatinib mesylate in a Chinese population"; Int J Hematol 89:445 (2009).

Satzger et al. "Anal Mucosal Melanoma with Kit-Activating Mutation and Response to Imatinib Therapy—Case Report and Review of the Literature"; Dermatology 220:77 (2010).

Russell "Hereditary Anemias of the Mouse: A Review for Geneticists"; Adv Genet 20:357 (1979).

Blackham, A., et al., "FPL 62064 , a topically active 5-lipoxygenase/cyclooxygenase inhibitor", Agents and Actions, vol. 30, No. 3-4, pp. 432-442, 1990, ISSN: 0065-4299.

Blackham, A., et al., "FPL 62064, a topically active 5-lipoxygenase/cyclooxygenase inhibitor", abstract, XP002725944, Database accession No. EMB-1990185513, Database Embase [Online] Elsevier Science Publishers, Amsterdam, N L;1990.

Amon, U., et al., "Mastocytosis—an update", JDDG: Journal Der Deutschen Dermatologischen Gesellschaft, vol. 8, No. 9, Jul. 30, 2010, pp. 695-712. XP055123925, ISSN: 1610-0379. DOI: 10.1111/j.1610-0387.2010.07482.x; EPO cited relevant pp. 707-710.

European Patent Office Extended Search Report, dated Jul. 4, 2014, European Application No. 12771047.3.

Rosenthal et al., "Quantitative assay of melanin in melanoma cells in culture and in tumors"; Anal Biochem 56:91 (1973).

Yarden et al., Human proto-oncogene c-kit a new cell surface receptor tyrosine kinase for an unidentified ; EMBO J, 6:3341-3351 (1987).

Blackham et al., "FPL 62064: A Novel Dual Inhibitor of Arachidonic Acid Metabolism in Skin"; Br J Pharmacol 95:536p (1988).

Chabot et al. "The proto-oncogene c-kit encoding a transmembrane tyrosine kinase receptor maps to the mouse W locus"; Nature 335:88 (1988).

Geissler et al. "The Dominant-White Spotting (W) Locus of the Mouse Encodes the c-kit Proto-Oncogene"; Cell 55:185 (1988).

Hearing et al. "Analysis of Mammalian Pigmentation at the Molecular Level";Pigment Cell Res 2:75 (1989).

Blackham et al. "FPL 62064, a topically active 5-lipoxygenase cyclooxygenase inhibitor" Agents Actions 30:432 (1990).

Zsebo et al. "Identification, purification, and biological characterization of hematopoietic stem cell factor from Buffalo rat liver"; Cell 63:195 (1990).

Zsebo et al. "Stem Cell Factor is Encoded at the SI Locus of the Mouse and is the Ligand for the c-kit Tyrosine Kinase Receptor" Cell 63:213 (1990).

Giebel et al."Mutation of the KIT (mast/stem cell growth factor receptor) protooncogene in human piebaldism"; Proc Natl Acad Sci U S A 88:8696 (1991).

Nishikawa et al. "1991 Nishikawa in utero manipulation of coat color formation by a monoclonal anti-c-kit antibody: two distinct waves of c-kit-dependency during melanocyte development"; EMBO J 10:2111 (1991).

Longley et al. "1993 Longley Altered metabolism of mast-cell growth factor (c-kit ligand) in cutaneous mastocytosis"; N Engl J Med 328:1302(1993).

Inoue et al."Coexpression of the c-kit receptor and the stem cell factor in gynecological tumors"; Cancer Res 54:3049 (1994).

Morita et al."Expression of c-kit ligand in human keratinocytes"; Arch Dermatol Res 286:273 (1994).

Spritz "Inhibition of Proliferation of Human Melanocytes by a Kit Antisense Oligodeoxynucleotide: Implications for Human Piebaldism and Mouse Dominant White Spotting (W)"; J Invest Dermatol 103:137S (1994).

Spritz et al. "Molecular basis of human piebaldism"; J Invest Dermatol 103:148 (1994).

Kitayama et al. "Constitutively Activating Mutations of c-kit Receptor Tyrosine Kinase Confer Factor-Independent Growth and Tumorigenicity of Factor-Dependent Hematopoietic Cell Lines"; Blood 85:790 (1995).

Luo et al. "Coordinated mRNA expression of c-Kit with tyrosinase and TRP-1 in melanin pigmentation of normal and malignant human melanocytes and transient activation of tyrosinase by Kit/SCF-R";Melanoma Res 5:303 (1995).

Nagata et al. "Identification of a point mutation in the catalytic domain of the protooncogene c-kit in peripheral blood mononuclear cells of patients who have mastocytosis with an associated hematologic disorder"; Proc Natl Acad Sci USA 92:10560 (1995).

Okura et al. "Effects of monoclonal anti-c-kit antibody (ACK2) on melanocytes in newborn mice"; J Invest Dermatol 105:322 (1995).

(56) References Cited

OTHER PUBLICATIONS

Reid et al. "Steel factor directs melanocyte development in vitro through selective regulation of the number of c-kit progenitors" Dev Biol 169:568 (1995).

Krystal et al. "Autocrine growth of small cell lung cancer mediated by coexpression of c-kit and stem cell factor"; Cancer Res 56:370 (1996).

Longley et al. "Somatic c-KIT activating mutation in urticaria pigmentosa and aggressive mastocytos; establishment of clonality in a human mast cell neoplasm"; Nat Genet 12:312 (1996).

Grichnik et al. "The SCF/KIT Pathway Plays a Critical Role in the Control of Normal Human Melanocyte Homeostasis"; J Invest Dermatol 111:233 (1998).

Hemesath et al. "MAP kinase links the transcription factor Microphthalmia to c-Kit signalling in melanocytes" Nature 391:298 (1998).

Hirota et al. "Gain-of-Function Mutations of c-kit in Human Gastrointestinal Stromal Tumors"; Science 279:577 (1998).

Imokawa et al. "Biological characterization of human fibroblast-derived mitogenic factors for human melanocytes"; Biochem J 330:1235 (1998).

Kunisada et al. "Transgene expression of steel factor in the basal layer of epidermis promotes survival, proliferation, differentiation and migration of melanocyte precursors"; Development 125:2915 (1998).

Kunisada et al. "Murine Cutaneous Mastocytosis and Epidermal Melanocytosis Induced by Keratinocyte Expression of Transgenic Stem Cell Factor"; J Exp Med 187:1565 (1998).

Price et al. "Lineage-specific Signaling in Melanocytes"; J Biol Chem 273:17983 (1998).

Nishimura et al. Regulation of E- and P-Cadherin Expression Correlated with Melanocyte Migration and Diversification; Dev Biol 215:155 (1999).

Tian et al. "Activating c-kit Gene Mutations in Human Germ Cell Tumors"; Am J Pathol 154:1643 (1999).

Clarys et al. "Skin color measurements: comparison between three instruments: the Chromameter®, the DermaSpectrometer® and the Mexameter®"; Skin Res Technol 6:230 (2000).

Longley et al. "A proposed classification of mastocytosis incorporating molecular genetics"; Hematol Oncol Clin North Am 14:697 (2000).

Wu et al. "c-Kit triggers dual phosphorylations, which couple activation and degradation of the essential melanocyte factor Mi"; Genes Dev 14:301(2000).

Hachiya et al. "The Paracrine Role of Stem Cell Factor/c-kit Signaling in the Activation of Human Melanocytes in Ultraviolet-B-Induced Pigmentation"; J Invest Dermatol 116:578(2001).

Joensuu et al. "Effect of the tyrosine kinase inhibitor STI571 in a patient with a metastatic gastrointestinal stromal tumor"; N Engl J Med 344:1052 (2001).

Kadono et al. "The Role of the Epidermal Endothelin Cascade in the Hyperpigmentation Mechanism of Lentigo Senilis"; J Invest Dermatol 116:571(2001).

Ning et al. "Signal transducer and activator of transcription 3 activation is required for Asp816 mutant c-Kit-mediated cytokine-independent survival and proliferation in human leukemia cells"; Blood 97:3559 (2001).

Tuveson et al. "STI571 inactivation of the gastrointestinal stromal tumor c-KIT oncoprotein: biological and clinical implications"; Oncogene 20:5054 (2001)

Alaluf et al. "The Impact of Epidermal Melanin on Objective Measurements of Human Skin Colour"; Pigment Cell Res 15:119 (2002).

Briganti et al. "Chemical and Instrumental Approaches to Treat Hyperpigmentation"; Pigment Cell Res 16:101 (2003).

Moss et al. "Hair Depigmentation Is a Biological Readout for Pharmacological Inhibition of KIT in Mice and Humans"; J Pharmacol Exp Ther 307:476 (2003).

Widlund et al. "Microphthalmia-associated transcription factor: a critical regulator of pigment cell development and survival"; Oncogene 22:3035 (2003).

Yoon et al. "Reconstituted 3-dimensional human skin of various ethnic origins as an in vitro model for studies of pigmentation"; Anal Biochem 318:260 (2003).

Hattori et al. "The Epidermal Stem Cell Factor Is Over-Expressed in Lentigo Senilis: Implication for the Mechanism of Hyperpigmentation"; J Invest Dermatol 122:1256 (2004).

Mizoguchi "Melanocyte Development: With a Message of Encouragement to Young Women Scientists"; Pigment Cell Res 17:533 (2004).

Pan et al. "KIT (CD117) is frequently overexpressed in thymic carcinomas but is absent in thymomas"; J Pathol 202:375 (2004).

Rönnstrand "Signal transduction via the stem cell factor receptor/c-Kit"; Cell Mol Life Sci 61:2535 (2004).

Reid et al. "Steel factor directs melanocyte development in vitro through selective regulation of the number o c-kit progenitors"; Dev Biol 169:568 (1995).

Longley et al. "Somatic c-Kit activationg mutation in urticria pigmentosa andaaggeressive mastocytosis; establishment of clonality in human mast cell neoplasm"; Nat Genet 12:312 (1996).

Longley "What dermatologists need to know about mast cell disease: A dermatopathologist's view"; Cutis 64:281 (1999).

Nishimura et al. Regulation of E- and P-Dadherin Expression Correlated with Melanocyte Migration and Diversification; Dev Biol 215:155 (1999).

* cited by examiner

USE OF N-(4-METHOXYPHENYL)-1-PHENYL-1H-PYRAZOL-3-AMINE AND RELATED COMPOUNDS

CROSS REFERENCE TO RELATED APPLICATIONS

This application claims priority from U.S. Provisional Application Ser. No. 61/448,080, filed on Mar. 1, 2011, which is incorporated herein by reference in its entirety.

FIELD OF THE INVENTION

This invention relates to inhibiting the activity of Kit receptor tyrosine kinase using compositions comprising N-(4-methoxyphenyl)-1-phenyl-1H-pyrazol-3-amine (FPL-62064) and related compounds, and to associated methods of treatment of conditions wherein the inhibition of the Kit kinase may be beneficial. This invention also relates to the treatment of skin disorders, such as hyperpigmentation and cutaneous mastocytosis, and to cosmetic uses such as skin lightening.

BACKGROUND OF THE INVENTION

Kit Kinase is a Biologically Important, Clinically Validated Drug Target

Kit and Kit-Ligand; Biological Role of Kit Signaling

The human receptor tyrosine kinase Kit (also referred to as c-Kit or stem cell factor receptor) was identified as the cellular homolog of the viral oncogene v-Kit [Yarden et al. (1987) EMBO J. 6:3341]. In 1988, the white spotting locus in the mouse was found to encode Kit gene, and subsequently a novel mast cell growth factor was identified as the ligand for the Kit receptor [Geissler et al. (1988) Cell 55:185, Chabot et al. (1988) Nature 335:88]. Soon thereafter, the coding sequence for the ligand of the Kit receptor was mapped to the steel locus in mice, and the protein was identified as a growth factor for hematopoietic stem cells [Zsebo et al. (1990) Cell 63:213, Zsebo et al. (1990) Cell 63:195]. Thus, Kit ligand is also known as mast cell growth factor, steel factor, and stem cell factor.

The Kit protein contains five immunoglobulin-like domains within its extracellular part, a single trans-membrane domain, and a tyrosine kinase domain within its intracellular part. Binding of the dimeric Kit-ligand to two Kit receptor molecules leads to receptor dimerization and activation of tyrosine kinase activity, the receptor becomes autophosphorylated at tyrosine residues, and the resulting phosphotyrosine residues serve as docking sites for signal transduction molecules containing phosphotyrosine-binding SH2 and PTB domains. Specific point mutations within the Kit sequence may also lead to ligand-independent activation of the receptor tyrosine kinase [Kitayama et al. (1995) Blood 85:790].

Kit receptor tyrosine kinase is expressed in a variety of cell types, including hematopoietic cells, melanocytes, mast cells, peripheral blood eosinophils, vascular smooth muscle cells, and epithelial cells [Reber et al. (2006) Eur J Pharmacol 533:327]. Kit participates in multiple signal transduction pathways mediated by various enzymes and adaptor proteins binding to phosphorylated Kit, including Ras/MAPK, Jak/STAT, and AKT pathways [Roskoski (2005) Biochem Biophys Res Commun 338:1307] which are involved in diverse biological responses, including chemotaxis, proliferation, differentiation and survival [Rönnstrand (2004) Cell Mol Life Sci 61:2535]. Kit signaling is important in erythropoiesis, lymphopoiesis, mast cell development and function, megakaryopoiesis, gametogenesis and melanogenesis [Rönnstrand (2004) Cell Mol Life Sci 61:2535].

Aberrant Activation of Kit is Involved in Malignancy

Aberrant activation of Kit tyrosine kinase is implicated in a number of cancers. In several tumor types, autocrine loops have been found, i.e. the tumors produce both Kit-ligand and Kit, leading to autonomous stimulation. These include small cell lung carcinomas, colorectal carcinoma, breast carcinoma, gynecological tumors and neuroblastomas [Krystal et al. (1996) Cancer Res 56:370, Inoue et al. (1994) Cancer Res 54:3049, Rönnstrand (2004) Cell Mol Life Sci 61:2535]. Overexpression of Kit has been implicated in the development of thymic carcinoma [Pan et al. (2004) J Pathol 202:375] and certain melanomas [Smalley et al. (2009) Histol Histopathol 24:643]. Gain-of-function mutations in Kit have been found in many cancers, including mast cell leukemia, acute myeloid leukemia [Ning et al. (2001) Blood 97:3559], germ cell tumors (seminomas and dysgerminomas) [Tian et al. (1999) Am J Pathol 154:1643], and certain subgroups of melanoma [Curtin et al. (2006) J Clin Oncol 24:4340], and gastrointestinal stromal tumors (GISTs) [Hirota et al. (1998) Science 279:577], as well as in mastocytosis [Longley et al. (1996) Nat Genet. 12:312, Nagata et al. (1995) Proc Natl Acad Sci USA 92:10560]. Activating Kit mutations are frequent in cutaneous mast cell tumors—most common skin tumor in dogs [Khanna et al. (2009) Clin Cancer Res 15:3645].

Kit Kinase is a Clinically Validated Drug Target for Several Pathologies

Imatinib is a small molecule protein kinase inhibitor originally developed as an Abl inhibitor for treatment of chronic myelogenous leukemia. The recognition of its inhibitory activity against Kit kinase, in addition to its original target, prompted investigations on the use, and subsequent demonstration of clinical effectiveness, of this agent for the treatment of gastrointestinal stromal tumor (GIST)—a malignancy characterized by the activation of Kit receptor [Tuveson et al. (2001) Oncogene 20:5054, Joensuu et al. (2001) N Engl J Med 344:1052, Imatinib FDA Label, 2009]. Additional small molecule Kit inhibitors, such as dasatinib and nilotinib, have been subsequently developed for the treatment of GIST. Further, identification of the role of Kit kinase in new pathological contexts led to demonstration of new utility for Kit inhibitors. Examples include: incontinence [Biers et al. (2006) BJU Int 97:612, Kubota et al. (2007) Hinyokika Kiyo 53:435], rheumatoid arthritis [Juurikivi et al. (2005) Ann Rheum Dis 64:1126, Vernon et al. (2009) J Clin Rheumatol 15:267, Eklund et al. (2008) J Clin Rheumatol 14:294], subgroups of melanoma [Smalley et al. (2009) Histol Histopathol 24:643], including mucosal melanoma [Satzger et al. (2010) Dermatology 220:77], and skin pigmentation disorders [Legros et al. (2005) Br J Dermatol 153:691]. Imatinib has also demonstrated efficacy in patients with systemic mastocytosis caused by activating Kit mutations [Gotlib (2006) Immunol Allergy Clin North Am 26:575]. It is now well appreciated by those skilled in the art that the use of Kit inhibitors should be considered in any pathology wherein Kit signaling is implicated.

Kit Kinase is a Highly Validated Target for Skin and Hair Depigmentation

As discussed in greater detail below, Kit is required for the maintenance and functioning of melanocytes (skin cells required for the development of pigmentation). Neutralizing antibodies against Kit produce reversible depigmentation in animals [Moss et al. (2003) J Pharmacol Exp Ther 307:476].

In humans, loss-of-function defects in Kit result in piebaldism, a spotted depigmentation disorder [Giebel et al. (1991) Proc Natl Acad Sci USA 88:8696]. Small molecule systemic inhibitors of Kit (e.g., oncology drugs imatinib and sunitinib) produce reversible skin and hair depigmentation in human patients as a side effect [Zhao et al. (2009) Int J Hematol 89:445]. Consequently, Kit represents a highly validated target for the development of new topical depigmenting agents.

Kit Kinase Inhibitors: New Treatment Options Needed

As noted above, Kit kinase is an important therapeutic target. Among the small molecule protein kinase inhibitors approved by the US Food and Drug Administration (FDA) since 2001, imatinib and at least five others inhibit Kit protein kinase. However, all these drugs are oncology drugs with significant side effects; and all of them are systemic drugs, while many diseases involving Kit kinase, such as diseases and disorders of the skin, could be effectively addressed locally. There is a clear need for safer Kit kinase inhibitor drugs, and in particular topical drugs, wherein reduced systemic exposure will reduce the potential for systemic toxicity, which is characteristic of the currently available inhibitors. The present invention addresses this and other needs by providing inhibitors of Kit kinase, including topically bioavailable inhibitors.

FPL-62064

FPL-62064 is a Fisons plc. (Ipswich, Suffolk, United Kingdom) development code for N-(4-methoxyphenyl)-1-phenyl-1H-pyrazol-3-amine. The compound and synthetic methods of preparing it are described in the U.S. Pat. No. 4,810,719 (incorporated herein by reference in its entirety, Issued: Mar. 7, 1989); the patent further discloses the use of 1,N-diarylpyrazol-3-amines, including FPL-62064, for treatment or prophylaxis of inflammatory conditions, including rheumatoid arthritis, osteoarthritis, and inflamed joints; eczema and psoriasis; conjunctivitis; and asthma. Related analogs are disclosed in the U.S. Pat. No. 5,428,044, incorporated herein by reference in its entirety.

FPL-62064 is reported to inhibit arachidonic acid metabolism via dual inhibition of 5-lipoxygenase (5-LO) and prostaglandin synthetase (PGS) enzymes. In in vitro assays, FPL-62064 inhibits 5-LO with $IC_{50}$ values of 3.5-11.5 µM, and PGS with $IC_{50}$ of 3.1 µM. In intact RBL-1 cells, 5-LO is inhibited with $IC_{50}$ of 31 µM, and PGS with $IC_{50}$ of 3.6 µM [Blackham et al. (1990) Agents Actions 30:432]. In animal testing, FPL-62064 inhibited UV irradiation-induced erythema and prostaglandin E2 formation in guinea pig, edema formation and eicosanoid production induced by arachidonic acid in the mouse ear, and also, when co-injected with arachidonic acid, edema and eicosanoid formation in rabbit skin. FPL-62064, injected intraperitoneally as a fine suspension in saline, demonstrated local activity against immune-complex-induced peritoneal inflammation in the mouse [Blackham et al. (1990) Agents Actions 30:432, Blackham et al. (1988) Br J Pharmacol 95:536p].

FPL-62064 is topically bioavailable, and, desirably for a topical drug, it is rapidly and extensively metabolized upon intravenous administration; it is inactive by the oral route at doses up to 200 mg/kg against carrageenin foot edema in rats [Blackham et al. (1988) Br J Pharmacol 95:536p, Blackham et al. (1990) Agents Actions 30:432]. 2% topical formulation of FPL-62064 had been in development by Fisons plc. in the 1980's and 1990's as a treatment for psoriasis. Blackham et al., citing preliminary data, reported the topical application of the drug to be safe and well tolerated in humans [Blackham et al. (1990) Agents Actions 30:432].

BRIEF SUMMARY OF THE INVENTION

There is a great need in the art to develop safe, effective, and locally, e.g. topically, bioavailable therapeutic agents to treat and prevent disorders, e.g., diseases or conditions, in particular those involving the skin, which may be treatable through Kit kinase inhibition; such diseases include hyperpigmentation, mastocytosis, and certain cancers. Furthermore, there is a great public demand for new means of achieving desirable cosmetic effects, such as improving beauty or decreasing the apparent age. The present invention addresses this and other needs by providing-compounds of formulas I, II, and III, described in the section "*Compounds for Use in the Methods of the Invention*" of the present disclosure, which are inhibitors of Kit kinase. A useful compound of the present invention is FPL-62064 (N-(4-methoxyphenyl)-1-phenyl-1H-pyrazol-3-amine).

The present disclosure describes methods for achieving a cosmetically desirable outcome in a subject in need thereof, comprising topically applying to skin of the subject a composition comprising an amount of a compound effective to reduce a level of pigmentation of the skin, wherein the compound is selected from compounds of formulae I, II, and III, and pharmaceutically acceptable salts, esters, and prodrugs thereof.

The present disclosure describes cosmetic compositions for topical application to skin, comprising an amount of a compound which is effective to reduce a level of pigmentation of the skin, wherein the compound is selected from compounds of formulae I, II, and III, and pharmaceutically acceptable salts, esters, and prodrugs thereof.

The present disclosure describes compounds for use in a cosmetic composition for topical application to skin, wherein the compound is selected from compounds of formulae I, II, and III, and pharmaceutically acceptable salts, esters, and prodrugs thereof.

The present disclosure describes uses of a compound in the manufacture of a cosmetic composition for topical application to skin, wherein the compound is selected from compounds of formulae I, II, and III, and pharmaceutically acceptable salts, esters, and prodrugs thereof.

The present disclosure describes compounds for use in reducing, or inhibiting the increase of, skin or hair pigmentation, for treating a skin pigmentation condition, or for treating cancer or mastocytosis in a subject in need thereof, wherein the compounds are selected from compounds of formulae I, II, and III below, and pharmaceutically acceptable salts, esters, and prodrugs thereof.

In certain implementations, the skin pigmentation condition contemplated herein is hyperpigmentation of the skin, such as periorbital hyperpigmentation, post-inflammatory hyperpigmentation, or drug-induced hyperpigmentation. In other exemplary implementations, the skin pigmentation condition is melasma, freckles, lentigines, café-au-lait macules, acanthosis nigricans, or nevi.

The present disclosure also describes use of compounds selected from compounds of formulae I, II, and III, and pharmaceutically acceptable salts, esters, and prodrugs thereof, in the manufacture of a medicament for reducing, or preventing the increase, of skin or hair pigmentation, for treating a skin pigmentation condition, or for treating for treating cancer or mastocytosis in a subject in need thereof.

The present disclosure also describes methods for reducing, or preventing the increase, of skin or hair pigmentation, for treating a skin pigmentation condition, or for treating for treating cancer or mastocytosis, comprising administering to a subject in need thereof an effective amount of a compound, wherein the compound is selected from compounds of formulae I, II, and III below, and pharmaceutically acceptable salts, esters, and prodrugs thereof.

The present disclosure describes compositions for reducing skin or hair pigmentation, or for preventing, reducing, or inhibiting the increase of such pigmentation, in a subject in need thereof. These compositions include a therapeutically or cosmetically effective amount of a compound of formula I, II, or III or a pharmaceutically acceptable salt, ester, or prodrug thereof. In one implementation, reducing skin or hair pigmentation using the compositions disclosed herein is practiced to achieve a desirable cosmetic effect.

In one implementation, the compositions comprising a compound of formula I, II, or III are applied to the skin of the subject in a pharmaceutically acceptable topical formulation. In certain implementations, the pharmaceutically acceptable topical formulation is a cosmetic formulation that includes cosmetically useful substances and components such as fragrances, antioxidants, amino acids, vitamins, coloration agents, including coloration blocking agents, sunscreens, thickeners, or gelling agents employed to confer pleasing tactile properties on the formulation, and the like.

The present disclosure also describes cosmetic compositions, and compositions for achieving a desirable cosmetic outcome or effect in a subject, that include a cosmetically effective amount of a compound of formula I, II, or III or a pharmaceutically acceptable salt, ester, or prodrug thereof.

In certain exemplary implementations, the desirable cosmetic effect is reducing, or inhibiting the increase of, skin pigmentation; in other words, whitening, evening, smoothing, clearing, lightening or brightening of skin tone; increasing fairness of complexion; increasing the extent to which skin tone or complexion resembles pearl, ivory, snow, silver, milk, alabaster and the like; bleaching or depigmenting the skin; or imparting appealing and attractive perceived quality referred to as radiance, luminance, gleam, or glow; or decreasing the appearance of aging or perception of aged skin; reduction or disappearance of visible blemishes, darkness, dullness, patchiness, or unevenness of the skin tone, and the like. In certain implementations, the desirable cosmetic effect is achieved through the prevention or inhibition of a cosmetically undesirable outcome, such as a perceived aging of the skin, dullness or unevenness of the skin tone, emergence of visible blemishes, and the like.

The present disclosure also describes compositions for achieving lightening (development of a lighter skin tone or coloration), and for preventing or inhibiting darkening (development of a darker skin tone or coloration), in a subject, including a cosmetically effective amount of a compound of formula I, II, or III or a pharmaceutically acceptable salt, ester, or prodrug thereof. In certain implementations, the compositions disclosed herein are used for achieving a cosmetically pleasing outcome, such as achieving a desirable lightening of the skin, or preventing or reducing or inhibiting a cosmetically undesirable outcome, such as darkening of the skin.

The present disclosure also describes compositions for treating skin pigmentation conditions in a subject in need thereof, including a therapeutically effective amount of a compound of formula I, II, or III, or a pharmaceutically acceptable salt, ester, or prodrug thereof.

In certain implementations, the compositions disclosed herein are applied to an area, e.g., a well-delineated area, such as an area of a visible lesion or a localized area of pigmentation, or an area where a lesion or an area of undesirable coloration or pigmentation is expected to emerge. In certain other implementations, the compositions disclosed herein are applied more broadly to the subject.

The present disclosure also describes compositions for treating cancer or mastocytosis in a subject in need thereof including a therapeutically effective amount of a compound of formula I, II, or III or a pharmaceutically acceptable salt, ester, or prodrug thereof. In certain implementations, the cancer is gastro-intestinal stromal tumor, germ cell tumor, or melanoma.

In one implementation, the formulation including a compound of formula I, II, or III is administered topically. In a further implementation, the formulation is administered by injection, e.g., intralesional injection. In one aspect, the formulation is an extended release formulation, e.g., a depot injectable formulation using a biodegradable gel matrix, providing the benefit of concentrated local action and a convenient administration schedule, such as once-weekly administration. The present disclosure further contemplates a treatment regimen combining local administration, e.g., by injection, with topical administration. Such combinations can include a transition, once the desired effect has been achieved, from a local administration by injection to a topical administration. The present disclosure further contemplates uses, or kits comprising compositions, wherein the compositions disclosed herein are used first in one concentration, quantity, or composition, e.g., a relatively higher concentration, and subsequently, such as after the desired effect has been achieved, in another concentration, quantity, or composition, e.g., a relatively lower concentration, so as to maintain the desired effect, such as therapeutic or cosmetic effect.

The present disclosure also describes the use of the inventive compounds and compositions in conjunction with a physical treatment modality, such as surgery, intense pulse light (IPL) treatment, ultrasound treatment, radio-frequency treatment, or a laser treatment, for prevention, mitigation or inhibition, or other treatment, of undesirable hyperpigmentation secondary to an application of a physical treatment modality. In certain implementations, the inventive compounds and compositions are applied to the subjects within 1 hour, 2 to 6 hours, 12 hours to one day, or a week prior to, or subsequent to, an application of a physical treatment modality. In certain implementations, the area treated with the inventive compounds or compositions is substantially the same area as that to which a physical treatment modality is applied. In certain implementations, the area treated with inventive compounds or compositions is the area of the skin exposed to the physical treatment modality while treating e.g. an underlying tissue. The present disclosure also describes the use of the inventive compounds and compositions in conjunction with a chemical treatment modality, such as chemical peels.

In a particular aspect, the present disclosure provides methods for inhibiting in a cell the activity of Kit kinase, the methods including contacting the cell with an effective inhibitory amount of a compound of formula I, II, or III or a pharmaceutically acceptable salt, ester, or prodrug thereof. In certain implementations, the cell is a melanoblast or melanocyte, a mast cell, or a cancer cell.

It will be apparent to one skilled in the art that all of the embodiments disclosed herein are merely examples within the scope of the present invention; and further, that all such example embodiments may be described in various ways while still remaining within the scope of the present invention, including in terms of the use of the inventive compounds for manufacture of a medicament, or a cosmetic, for treatment of any of the conditions contemplated herein, or for the achievement of any desirable cosmetic effects contemplated herein; or in terms of compositions comprising the inventive compounds; or in terms of methods of use of the inventive compounds for treatment of any of the diseases contemplated herein, or for the achievement of any desirable cosmetic effects contemplated herein; and that the inventive compounds are also contemplated herein as compounds for use in treatment of any of the diseases contemplated herein, or for the treatment of any cosmetically or esthetically undesirable states or conditions contemplated herein.

In any of the implementations described herein, including compositions for cosmetic use, for reducing skin or hair pigmentation, for treating skin pigmentation disorders, and for treating cancer or mastocytosis, the compound of formula I, II, or III can be FPL-62064 as defined herein.

DETAILED DESCRIPTION

The present inventions are based, at least in part, on the unexpected discovery that FPL-62064, a topically active drug, previously in development as a treatment for psoriasis, is a potent inhibitor of Kit kinase. As disclosed in Example 1, in a biochemical assay, FPL-62064 inhibits Kit kinase with $IC_{50}$ of 6.89 µM (2 µg/ml). Further, FPL-62064 inhibits autophosphorylation of Kit in M07e cells with $IC_{50}$ of 1.2 µM (0.3 µg/ml). Thus, Kit kinase is inhibited by FPL-62064 at a low and clinically relevant concentration. As discussed in the Background and Exemplary Diseases sections, Kit protein kinase is important in the pathogenesis of various diseases, including but not limited to certain cancers and mastocytosis. For example, Kit is important for skin hyperpigmentation: kinase inhibitor drugs active against Kit (such as oncology chemotherapeutics imatinib and sunitinib) have caused reversible skin and hair depigmentation in human patients as a side effect, and neutralizing antibodies against Kit produce reversible depigmentation in animals (see e.g. Moss et al. (2003) J Pharmacol Exp Ther 307:47). Accordingly, the present invention provides, inter alia, that pharmaceutical compositions of FPL-62064 and related compounds in Formulas I, II, and III are valuable for the prevention, inhibition, or treatment of disorders and diseases, and in particular skin disorders and diseases, where Kit signaling plays a role, e.g., a critical role, such as certain cancers, mastocytosis, and hyperpigmentation. Since FPL-62064 is effective upon topical administration, clinical use of this and related compounds for topically treating hyperpigmentation and other diseases, as well as for cosmetic applications contemplated herein, will be associated with fewer side effects than the use of currently approved systemic Kit inhibitors such as imatinib.

Furthermore, the present invention is based, at least in part, on the discovery that FPL-62064 reduces skin pigmentation in human subjects, as described in Example 3. Accordingly, without necessarily adhering to a particular mechanism of action for FPL-62064, the present invention includes the concept that the various compositions disclosed herein, comprising FPL-62064 and/or related compounds in Formulas I, II, and III, are useful for achieving desirable changes in pigmentation, or preventing or inhibiting undesirable changes in pigmentation, as is more fully provided elsewhere in the present disclosure.

Even subtle characteristics of the pigmentation of a person's body surface play an important role in forming the overall impression of that person in the mind of the observer; for example, uneven pigmentation of the skin may make the person appear prematurely aged, and possibly less attractive. Accordingly, because of their utility with respect to pigmentation, the compounds described herein are useful for achieving the desirable cosmetic effect with respect to a body surface of a person, e.g., when used in topical cosmetic compositions. The desirable cosmetic effects contemplated by the present inventions may be referred to by various terms commonly used in the field of beauty and cosmetics, such as brightening the skin, reducing the perceived age or providing a younger or more lively appearance, or by even more general terms such as "improving" the appearance or making the skin appear "more beautiful"; it will be apparent to a skilled artisan that these and others are interchangeable terms referring to particular aspects of the cosmetically desirable appearance (e.g., "brightening" or "evening out") or directly to the desired cosmetic outcome perceived in its entirety ("youth" or "beauty"). Accordingly, the present invention is not limited to achieving "whitening" or the like, but also more generally refers to achieving, with respect to the body surface of a subject, a subjectively desirable outcome using the methods and compositions disclosed herein. It will be apparent to a skilled artisan that the present disclosure encompasses reduction, inhibition, prevention, or mitigation of cosmetically undesirable outcomes, such as the development of excessive or uneven pigmentation of the body surface, for instance as the consequence of passage of time, exposure to sunlight, or friction.

The present invention contemplates the use of FPL-62064 and related compounds within Formulas I, II, and III at various levels of purity consistent with their safe and effective use, e.g., in essentially pure form. The use of various hydrate or non-covalent complex forms of the compounds described herein is likewise contemplated, as is the use of all of their crystal, polymorph, and like forms. The compounds described herein can be used as solutions, or in various other forms, e.g., in various coarser or finer solid or partially solid forms, such as micronized or nanodispersion forms.

FPL-62064 is a 1,N-diaryl pyrazole-3-amine having the Following Formula

As disclosed herein, Kit receptor tyrosine kinase is inhibited by FPL-62064 at a compound concentration of 6.89 nM (2 µg/ml)—similar to the compound concentrations needed to inhibit 5-lipooxigenase and prostaglandin synthetase, the previously known targets of the drug. As disclosed herein, in the context of topical application, 2%, 4%, and 8% formulations of FPL-62064 caused statistically significant decrease of melanin index (a measure of the melanin content) in the human skin. The present discoveries of the activity of FPL-62064 against Kit receptor tyrosine kinase at low micromolar compound concentrations, and of the effect of FPL-62064 on skin pigmentation in humans, open new areas of important pharmaceutical and cosmetic applications for this and related compounds.

Definitions

The following definitions are provided for clarity and illustrative purposes only, and are not intended to limit the scope of the invention.

The term "alkyl" refers to a linear or branched hydrocarbon chain radical consisting solely of carbon and hydrogen atoms, containing no unsaturation, having from one to eighteen carbon atoms, and which is attached to the rest of the molecule by a single bond, e.g., methyl, ethyl, n-propyl, 1-methylethyl (isopropyl), n-butyl, n-pentyl, and 1,1-dimethylethyl(tert-butyl). Preferably, the alkyl will have 1-6 carbon atoms. The alkyl may be a cyclic alkyl such as a cyclopropyl or cyclobutyl. The term "$C_{1-6}$ alkyl" refers to an alkyl chain having 1 to 6 carbon atoms, and analogous subscripted terms such as "$C_{1-3}$ alkyl" or "$C_{1-18}$ alkyl" refer to alkyl chains ranging in the number of carbon atoms from the lower subscript to the higher subscript, inclusive.

The term "aryl" refers to an aromatic carbocyclic radical from 6 to 12 carbons, and which is attached to the rest of the molecule by a single bond, e.g., phenyl, 1-naphthyl, 2-naphthyl and the like. The aryl may be optionally substituted with one or more halogen, alkyl, alkoxy, hydroxy, carboxy (—$CO_2H$), carboalkoxy (—$CO_2$alkyl), amino, alkylamino (—NH-alkyl), or dialkylamino (—N(alkyl)$_2$) groups.

The term "alkanoyl" refers to an alkylacyl (—C(=O)-alkyl) radical, which is attached to the rest of the molecule by a single bond, e.g., acetyl (—C(=O)$CH_3$), propanoyl (—C(=O)$CH_2CH_3$), 3-methylbutanoyl (—C(=O)$CH_2CH(CH_3)_2$), and the like. The term "$C_{1-18}$ alkanoyl" refers to an alkanoyl chain having 1 to 18 carbon atoms.

The term "alkoxy" refers to linear or branched hydrocarbon chain radical consisting solely of carbon and hydrogen atoms, containing no unsaturation, having from one to eighteen carbon atoms, said carbon radical being attached to an oxygen atom. The oxygen atom is the point of attachment of the alkoxy radical to the rest of the molecule by a single bond, e.g., methoxy, ethoxy, n-propoxy, 1-methylethoxy(isopropoxy), n-butoxy, n-pentoxy, and 1,1-dimethylethoxy(tert-butoxy).

The term "trihalomethyl" refers to a methyl radical which is substituted by up to three halogen atoms, e.g., fluoromethyl, difluoromethyl, trifluoromethyl, chlorofluoromethyl, dichloromethyl, iodomethyl, dibromomethyl and the like.

Kit (NCBI GeneID: 3815) is also known in the art by other identifiers, including v-kit Hardy-Zuckerman 4 feline sarcoma viral oncogene homolog, mast/stem cell growth factor receptor, SCFR, proto-oncogene tyrosine-protein kinase KIT, c-KIT, and CD117 antigen. The nucleotide and amino acid sequences representing the human Kit are set forth in GenBank Accession numbers NM_000222 and N_000213, respectively. Animal species contemplated in the present invention are not limited to human; nucleotide and amino acid sequences representing Kit in other animal species can be readily retrieved, e.g. from NCBI GenBank, by anyone skilled in the art. The present invention further contemplates, without limitation, alternative transcript forms (such as splice variants) and mutant forms of Kit, and any corresponding protein isoforms, that may be further modified post-translationally, wherein such proteins have a kinase activity and can be inhibited by the compounds of formula I, II, or III. In the present disclosure, "Kit kinase" is used synonymously with Kit, but further highlights the enzymatic kinase activity of Kit, or the portion of Kit protein possessing that activity, as will be clear from the context to one skilled in the art.

Kit-ligand (NCBI GeneID: 4254), the cognate ligand of Kit, is also known in the art by other identifiers, including KITLG, steel factor, stem cell factor, SCF, mast cell growth factor, and MGF. The nucleotide and amino acid sequences representing the human Kit-ligand are set forth in GenBank Accession numbers NM_000899 and NP_000890, respectively. Animal species contemplated in the present invention are not limited to human; nucleotide and amino acid sequences representing Kit-ligand in other animal species can be readily retrieved, e.g. from NCBI GenBank, by anyone skilled in the art. The present invention further contemplates, without limitation, alternative transcript forms (such as splice variants) and mutant forms of Kit-ligand, and any conesponding protein isoforms, that may be further modified post-translationally, wherein such proteins are capable of activating Kit kinase.

The terms "disease", "disorder", and "condition", and terms with similar meanings, are used interchangeably, each of them or any combination of several of them encompassing the entire range of undesirable states, including, for example, grave diseases as well as merely cosmetically undesirable or inconvenient conditions, unless the context clearly states otherwise. In relation to any of the conditions recited herein, the terms "treat", "treatment", and the like mean to reduce, inhibit, or eliminate at least one symptom associated with such condition, or to arrest, slow, or reverse the progression of such condition, or to delay the onset and/or prevent, inhibit, or reduce the risk of developing or worsening of the condition.

The term "cosmetic composition" refers to compositions intended to create, enhance, improve, or restore, or to prevent or inhibit a deterioration or diminution in, beauty, aesthetics, appearance, or attractiveness of the body surface including the hair, as perceived visually, or through the senses of smell or touch, encompassing compositions intended for enhancing, altering or reducing the odor of a person, and compositions intended to enhance or modify the tactile feel of the body surface or hair; and further encompassing compositions intended for cleansing.

The phrase "cosmetically desirable outcome" refers to creating, enhancing, improving, or restoring, or to preventing or inhibiting a deterioration or diminution in, beauty, aesthetics, appearance, or attractiveness, or apparent health or youthfulness, of the body surface including the hair, as perceived visually, or through the senses of smell or touch; and further refers to decreasing the appearance of aging or perception of aged skin; and further encompassing cleansing.

Objective assessment of the skin color, e.g. of individual pigmented lesions or normal skin, can be performed, e.g., by measurements with a spectrophotometer CM-2600d (Konica Minolta, Osaka, Japan). This hand-held instrument utilizes the CIE L*a*b* color system. Color is quantified using the 3-digit output L*, a*, b*, where L* measures skin reflectance or lightness on a grey scale with values from 0 to 100 where 0 is black and 100 is white. The total epidermal melanin content is highly correlated with the L* values in human skin [Alaluf et al. (2002) Pigment Cell Res 15:119]. Increasing L* value corresponds to lightening of the skin [Brazzelli et al. (2006) Pediatr Dermatol 23:175].

Objective assessment of the skin color, e.g. of individual pigmented lesions, or of normal skin, can also be performed, e.g., by measurement of melanin index in the human skin, for example using the Mexameter® MX18 instrument (Courage & Khazaka, Cologne, Germany) [Clarys et al. (2000) Skin Res Technol 6:230]. For an example of using this instrument, see e.g. Huh et al. (2010) Ann Dermatol 22:21.

Objective assessment of skin lightening may also be conducted visually ("visual assessment" or "visual scoring") by having a licensed dermatologist or another trained observer record, using a scale such as 0 through 4 wherein 0 means no change and 4 means the perfect or maximal possible effect, the condition of the treated area, optionally in comparison with an untreated area, at periodic intervals, e.g. weekly; see Example 3.

The amount of melanin (melanin content) in a sample, such as in a skin sample or a hair sample, can be determined e.g. using an assay described in [Rosenthal et al. (1973) Anal Biochem 56:91], using a standard curve obtained with known quantities of synthetic melanin. Melanin may also be detected and quantified according to the method of Fontana-Masson (e.g. as described in [Yoon et al. (2003) Anal Biochem 318: 260]).

The terms "effective inhibitory amount" or "effective amount" when referring to the amounts of an inhibitor of a kinase is the amount of a compound sufficient to inhibit the activity of the kinase by at least 25%. Kinase activity inhibition can be measured using any method known in the art, for example using a radiometric filter binding assay, such as a Millipore KinaseProfiler assay.

The term "topical" with respect to treatment, composition, formulation, and the like means applied to, or intended for external application to, body surfaces, including the skin; mucous membranes, e.g. those of the vagina, anus, mouth or throat, eyes and ears; hair; nails and teeth.

The term "cosmetically effective" applied to dose or amount refers to that quantity of a compound of formula I, II, or III or a pharmaceutical composition including such compound, that is sufficient for a cosmetically beneficial or desirable effect following its administration to a subject.

The phrase "effective to reduce a level of pigmentation of the skin", and the phrase "cosmetically effective", or the term "effective", when used with respect to skin lightening, or with respect to reducing, or inhibiting the increase, of skin or hair pigmentation, refer to dose or amount that is sufficient to cause, following administration to a subject, or to an in vitro model, for a suitable observation period (such as, for a subject, 1 week, 4 weeks, 1 month, 2 months, or more; or for in vitro model, 1 hour, 6 hours, 12 hours, 1 day, 3 days, or more), a change in the skin or hair pigmentation according to any objective assessment method known in the art, with respect to skin or hair, as appropriate, for example: the increase in L* value of at least 1 unit; decrease in the melanin index value of at least 5%, or at least 10 units; or achieving, in objective visual assessment of skin pigmentation, the reading of at least 2 on the scale of 0 to 4; or a decrease of melanin content by at least 5%. Skin models, e.g. three-dimensional reconstituted skin models such as MelanoDerm (MatTek Corp., Ashland, Mass.), may be used. With respect to preventing or inhibiting the increase of pigmentation, the dose or amount is determined relative to an increase in pigmentation in the absence of treatment.

The cosmetic effect can be, for example, improving the physical appearance and/or aesthetics. The cosmetically effective amount of the composition may vary with the particular site being treated, the age and physical condition of the subject, the severity of the condition, the duration of the treatment, the nature of concurrent therapy, the specific compound or other active ingredients employed, the particular carrier utilized, and like factors well known in the art.

The phrase "therapeutically effective", and, when used with respect to treating a disease or condition, the term "effective", applied to dose or amount, refer to that quantity of an inventive compound, or a pharmaceutical composition containing such compound, that is sufficient to treat a disease or condition contemplated in the present invention, following its administration to an animal in need thereof.

The phrase "pharmaceutically acceptable", as used in connection with the compositions of the invention, refers to molecular entities and other ingredients of such compositions that are physiologically tolerable and do not typically produce untoward reactions when administered to a mammal (e.g., a human). Preferably, the term "pharmaceutically acceptable" means approved by a governmental regulatory agency or listed in the U.S. Pharmacopeia or other generally recognized pharmacopeia for use in mammals, and more particularly in humans.

The term "ester" refers to chemical compounds derived by reacting an oxoacid with a hydroxyl compound such as an alcohol or phenol. Esters are usually derived from an inorganic acid or organic acid in which at least one —OH (hydroxyl) group is replaced by an —O-alkyl(alkoxy) group, and most commonly by condensing a carboxylic acid with an alcohol. Esters useful with inventive compounds include e.g. esters formed by reacting an inventive compound having a hydroxyl group with a carboxylic acid used in the art for forming pharmaceutically acceptable salts.

The term "prodrug" means a compound, that is transformed in vivo to yield an inventive compound, including an ionized moiety, salt, hydrate or solvate thereof. The transformation may occur by various mechanisms known in the art, as discussed e.g. in Design of prodrugs. Bundgaard H, eds. Amsterdam: Elsevier 1985; Bioreversible Carriers in Drug Design, ed. Edward B. Roche, Pergamon Press, 1987; Prodrugs. Stella V J et al., eds. New York: Springer 2007, and in Prodrugs and Targeted Delivery. Mannhold R et al., eds. Weinheim: Wiley-VCH 2011. Further examples of prodrug design approaches useful with inventive compounds for topical delivery in particular can be found in Sloan et al. (2006) Pharm Res 23:2729, Sloan et al. (2003) Med Res Rev 23:763, and in Prodrugs: topical and ocular drug delivery. Sloan K B, ed. New York: M. Dekker 1992; ester, N-acyl and soft N- and S-alkyl derivatives are examples of prodrugs contemplated herein.

The compounds of the present invention can be administered locally or systemically. The term "local" refers to a route of administration includes, for example, topical, intradermal, subepidermal, mucosal, intraoral, by inhalation, transdermal, transmucosal, intralesional, intravitreal, rectal, vaginal, otic, and intranasal, and oral administration of a compound in an bioadhesive oral formulation targeting the gastrointestinal tract. Local administration is used with the intent to achieve concentrated local action of the drug and prevent, reduce, or delay systemic exposure of the drug. The term "systemic" refers to a route of administration includes, for example, parenteral administration such as intravenous or intraarterial, oral, transdermal, transmucosal, intranasal, and buccal administration, intended to deliver the drug into the systemic circulation. Parenteral administration includes subcutaneous, intravenous, intramuscular, intra-articular, intrasynovial, intraperitoneal, intrahepatic, and intracranial administration.

A preferred route of administration according to the present invention will depend primarily on the indication being treated and includes, among others, topical, mucosal, intraoral, by inhalation, transdermal, transmucosal, intralesional, intradermal using a depot injectable formulation, intravitreal, rectal, vaginal, otic, and intranasal administration.

The term "about" means within an acceptable error range for the particular value as determined by one of ordinary skill in the art, which will depend in part on how the value is measured or determined. For example, "about" can mean within an acceptable deviation or error, per the practice in the art. Alternatively, "about" can mean a range of up to ±10%, of a given value. Alternatively, particularly with respect to biological systems or processes, the term "about" can mean within 3.16-fold of a value. Where particular values are provided herein, unless otherwise stated, the term "about" is implicit.

The terms "subject", "patient" and the like are used interchangeably and mean, unless the context clearly dictates otherwise, any animal, including mammals. In particular, the term may refer to a human, a non-human primate, a bovine, an ovine, an equine, a porcine, a canine, a feline, or a rodent such as mouse or rat.

As used in this specification and the appended claims, unless the context clearly dictates otherwise, the singular forms "a," "an," and "the" include plural references; the masculine, neuter, or feminine forms refer to either or all; and the use of "or" in lists and the like is inclusive. Expressions such as "including", "for example", "such as" and the like, and any reference to an "example" and the like, introduce non-limiting examples. "Inventive" compounds, compositions and the like refer to those of the present invention.

Compounds for Use in the Methods of the Invention

The present inventions provide the use of the compounds of formula I having the following structure:

Formula I wherein
$R^1$ is selected from H, $OR^6$, alkyl, and aryl;
$R^2$ is selected from H, alkyl, and aryl;
each $R^3$, $R^4$ and $R^5$ is independently selected from H, $N(R^6)_2$, $OR^6$, $CON(R^6)_2$, $CO_2R^6$, $COR^6$, alkyl, and aryl;
each $R^6$ is independently selected from H, alkyl, and aryl;
i is 0, 1, 2, 3, 4, or 5;
j is 0, 1, or 2; and
k is 0, 1, 2, 3, or 4;

The inventions further encompass the use of the compounds of formula II having the following structure:

Formula II wherein
$R^7$ is selected from H, $C_{1-18}$ alkyl, and $C_{1-18}$ alkyl substituted by Ar;
each $R^8$ and $R^9$ is independently selected from halogen, hydroxy, —CN, —$COR^{11}$, trihalomethyl, alkoxy, alkoxy substituted by —$COR^{11}$, alkoxy substituted by —$NR^{12}R^{13}$, $C_{1-18}$ alkyl, $C_{1-18}$ alkyl substituted by —$COR^{11}$, $C_{1-18}$ alkyl substituted by —$NR^{12}R^{13}$, alkoxy substituted by Ar, —OC(=O)$C_{1-18}$ alkyl, —S(O)$_p$—$C_{1-18}$ alkyl, —S(O)$_p$Ar, —$NR^{12}R^{13}$, and —OAr;
each $R^{10}$ is independently selected from H, halogen, Ar, $C_{1-18}$ alkyl and $C_{1-18}$ alkyl substituted by Ar;
each $R^{11}$ is selected from H, $C_{1-18}$ alkyl, —$OR^{14}$, and —$NR^{12}R^{13}$;
each $R^{12}$ and $R^{13}$ is independently selected from H, $C_{1-18}$ alkyl, $C_{1-18}$alkanoyl, and Ar;
each $R^{14}$ is independently selected from H, $C_{1-18}$ alkyl, or Ar;
each Ar is independently phenyl or naphthyl;
l is 0, 1, 2, 3, 4, or 5;
m is 0, 1, or 2;
n is 0, 1, 2, 3, 4 or 5; and
p is 0, 1 or 2;

The inventions further encompass the use of the compounds of formula III having the following structure:

Formula III wherein
R$^{15}$ is selected from H, and C$_{1-3}$ alkyl;
R$^{16}$ is selected from H, C$_{1-18}$ alkyl, Ar$^1$, —C(=O)C$_{1-18}$ alkyl, C$_{1-18}$ alkyl substituted by —COR$^{20}$, C$_{1-18}$ alkyl substituted by —NR$^{21}$R$^{22}$, and C$_{1-18}$ alkyl substituted by Ar$^1$;
each R$^{17}$ and R$^{19}$ is independently selected from halogen, hydroxy, —COR$^{20}$, trihalomethyl, alkoxy, alkoxy substituted by —COR$^{20}$, C$_{1-18}$ alkyl, and C$_{1-18}$ alkyl substituted by —NR$^{21}$R$^{22}$;
each R$^{18}$ is independently selected from H, halogen, Ar$^1$, C$_{1-18}$ alkyl, and C$_{1-18}$ alkyl substituted by Ar$^1$;
each R$^{20}$ is independently selected from H, C$_{1-18}$ alkyl, —OR$^{23}$, and —NR$^{21}$R$^{22}$;
each R$^{21}$ and R$^{22}$ is independently selected from H, C$_{1-18}$ alkyl, C$_{1-18}$ alkanoyl, and Ar$^1$;
each R$^{23}$ is independently selected from H, C$_{1-18}$ alkyl, and Ar$^1$;
each Ar$^1$ is independently phenyl or naphthyl;
q is 0, 1, 2, 3, 4, or 5;
r is 0, 1, or 2; and
s is 0, 1, 2, 3, or 4.
A specific compound of the present invention is as follows:

FPL-62064, N-(4-methoxyphenyl)-1-phenyl-1H-pyrazol-3-amine

Also encompassed herein are pharmaceutically acceptable salts, prodrugs, esters, and isomers of the compounds of the present invention, and their various hydrate and coordination forms.

In some preferred embodiments, the compound of formula I, II, or III is in the form of a "pharmaceutically acceptable salt" thereof; the foregoing term refers to non-toxic salts of the inventive compounds which are generally prepared by reacting the free base with a suitable organic or inorganic acid or by reacting the acid with a suitable organic or inorganic base. Representative salts include hydrochloride, sulfate, borate, nitrate, acetate, phosphate, oxalate, oleate, laurate, stearate, palmitate, valerate, benzoate, naphthylate, mesylate, tosylate, citrate, lactate, maleate, succinate, tartrate, fumarate, and the like; see e.g. Berge et al. (1977), J Pharm Sci 66:1.

Also included within the scope of the invention are the individual isomers of the compounds represented by formula I, II, or III as well as any wholly or partially equilibrated mixtures thereof. Certain inventive compounds are capable of existing in stereoisomeric forms (e.g. diastereomers and enantiomers) and the invention extends to each of these stereoisomeric forms and to mixtures thereof including racemates. The different stereoisomeric forms may be separated one from the other by known methods, or any given isomer may be obtained by stereospecific or asymmetric synthesis. The invention also extends to any tautomeric forms and mixtures thereof.

Compounds of the invention can be prepared by the methods described in U.S. Pat. Nos. 4,810,719 and 5,428,044, both of which are incorporated herein by reference in their entirety.

Exemplary Diseases

Provided herein are methods and compositions useful for treating or preventing diseases or conditions wherein the inhibition of Kit kinase may be beneficial, and particularly for the treatment or prevention of skin diseases or conditions. Without limiting the generality of the present invention, the diseases or conditions contemplated herein include skin hyperpigmentation, excessive or unwanted skin and hair pigmentation, mastocytosis, and cancers of different organs wherein Kit signaling plays a critical role. Selected examples of the diseases treatable using the compounds of the invention are discussed in detail below.

Skin Hyperpigmentation, Excessive or Unwanted Skin and Hair Pigmentation

Melanin, a pigment that determines the coloration of human skin, is produced by cells known as melanocytes. Melanocytes produce melanin in organelles called melanosomes. Melanosomes are transferred from melanocytes to keratinocytes, a layer of keratin-producing cells that is closer to the outer surface of the skin. The more melanin is produced, and the more melanosomes are transferred to the keratinocytes, the darker the skin appears. This process can be altered in persons of any skin type or race. Alteration that results in excessive darkening is known as hyperpigmentation. The color of human hair is the result of a similar process of transfer of melanin granules from the melanocytes resident in the hair follicles.

Existing anti-pigmentation agents such as hydroquinone, retinoids, ascorbic acid, and kojic acid have limited efficacy and a number of undesired effects including potential carcinogenicity, skin irritation, and skin sensitization. Hydroquinone remains the most widely used skin-lightening agent, but its safety profile makes it controversial [Briganti et al. (2003) Pigment Cell Res 16:101, Draelos (2007) Dermatol Ther 20:308]. New therapeutic agents are needed.

Kit and Kit Ligand Play a Fundamental Role in Melanocyte Biology and Pigmentation The interacting pair of receptor tyrosine kinase Kit, and its ligand molecule, referred to herein as Kit-ligand, was originally characterized as a pair of mouse coloration mutants—white spotting (W) and steel (Sl), respectively. These mutations specifically affect the fate and survival of neural crest derived melanocytes [Russell (1979) Adv Genet. 20:357]. Homozygous mutants exhibit a characteristic black-eyed/white-coat phenotype, while heterozygous animals demonstrate diluted coat color with a particular steel-like appearance and white spots on forehead and belly.

In humans, the heterozygous mutation of the Kit gene results in the pigmentation disorder piebaldism, sometimes referred to as partial albinism [Giebel et al. (1991) Proc Natl Acad Sci USA 88:8696, Spritz (1994) J Invest Dermatol 103:137 S]. Affected individuals exhibit unpigmented congenital patches of skin and hair from which melanocytes are completely absent.

In the mouse, null mutations at the Kit or Kit-ligand locus block migration as well as survival of melanocyte precursors [Mizoguchi (2004) Pigment Cell Res 17:533]. Adult mouse epidermis does not express Kit-ligand and has no melanocytes; melanocytes are exclusively localized to the hair bulb, and thus the mouse has unpigmented skin but pigmented fur [Nishimura et al. (1999) Dev Biol 215:155].

In contrast to the mouse, Kit-ligand is expressed in the adult human epidermis, where it plays an important role in the homeostasis of epidermal, Kit receptorexpressing melanocytes [Grichnik et al. (1998) J Invest Dermatol 111:233, Spritz et al. (1994) J Invest Dermatol 103:148]. Both human keratinocytes and fibroblasts secrete Kit-ligand [Morita et al. (1994) Arch Dermatol Res 286:273, Imokawa et al. (1998) Biochem J 330:1235]. The injection of Kit or Kit-ligand blocking antibodies into human skin explants grafted on nude mice results in the loss of melanocytes. On the contrary, injection of the soluble form of Kit-ligand causes hyperpigmentation of the explanted skin tissue [Grichnik et al. (1998) J Invest Dermatol 111:233]. Similarly, forced expression of Kit-ligand in mouse epidermis prevents the loss of epidermal melanocytes, resulting in highly pigmented epidermis [Nishimura et al. (1999) Dev Biol 215:155, Kunisada et al. (1998) J Exp Med 187:1565, Kunisada et al. (1998) Development 125:2915]. This suggests that in both mice and humans, epidermal melanocytes require a constant keratinocyte-derived Kit-ligand stimulation for their maintenance.

The crucial role of the Kit-ligand/Kit pathway for developing murine melanocytes was further demonstrated using an anti-Kit-ligand antibody ACK2. This antibody blocks the ability of Kit ligand to activate Kit and leads to the disappearance of melanocytes [Nishikawa et al. (1991) EMBO J. 10:2111, Okura et al. (1995) J Invest Dermatol 105:322, Reid et al. (1995) Dev Biol 169:568]. The regeneration of melanocytes, presumably from Kit-independent melanocyte stem cells, begins after about a month after ceasing the ACK2 treatment [Kunisada et al. (1998) Development 125:2915].

Kit-ligand/Kit signaling is also critically involved in the biologic mechanism of pigmentation. For instance, in the course of ultraviolet (UV)-B-induced pigmentation of brownish guinea pig skin, the subepidermal injection of Kit inhibitory antibodies completely abolished the induction of pigmentation in the UV-B-exposed area [Hachiya et al. (2001) J Invest Dermatol 116:578].

Mechanism of Kit Influence on Pigmentation

Kit receptor signaling is believed to control pigmentation via modulation of MITF [Hemesath et al. (1998) Nature 391:298; Price et al. (1998) J Biol Chem 273:17983; Wu et al. (2000) Genes Dev 14:301]; MITF is a key transcription factor controlling the expression of several enzymes in the pigment biosynthesis pathway, including tyrosinase [Widlund et al. (2003) Oncogene 22:3035], which catalyzes rate-limiting steps in melanin synthesis [Hearing et al. (1989) Pigment Cell Res 2:75]. Addition of Kit-ligand is known to cause an increase of tyrosinase activity, e.g. in melanoma cell lines [Luo et al. (1995) Melanoma Res 5:303].

Kit Inhibitor Drugs Cause Skin and Hair Depigmentation in Humans

There is now an overwhelming amount of evidence demonstrating that Kit inhibitor drugs (imatinib as well as newer Kit inhibitors such as dasatinib, sunitinib, and pazopanib) influence skin and hair pigmentation of patients; see e.g. Arora et al. (2004) Ann Oncol 15:358; Sharma et al. (2005) Indian J Dermatol Venereol Leprol 71:45; Deshmukh et al. (2005) J Assoc Physicians India 53:291; Sunita et al. (2006) Indian J Pharmacol 38:66; Leong et al. (2004) Cancer 100: 2486-7; and Zhao et al. (2009) Int J Hematol 89:445. Skin depigmentation and hypopigmentation side effects upon treatment with Kit inhibitor drugs are very prevalent in ethnically pigmented patients, with reported incidence near 80% in some studies. In light-skinned patients, skin depigmentation is usually noted in connection with depigmentation of hair, with reported incidence exceeding 60% (e.g., [Faivre et al. (2006) J Clin Oncol 24:25]), or in connection with preexisting hyperpigmented lesions [Campbell et al. (2009) Arch Dermatol 145:1313; McPartlin et al. (2005) Br J Haematol 129:448].

Melasma

Melasma is a common acquired symmetric hypermelanosis characterized by irregular light brown to gray-brown macules involving the face, and, occasionally, other sun-exposed areas including the forearms and back. Melasma is a consequence of specific hyper-functional melanocytes that cause excessive melanin deposition in the epidermis and dermis [Grimes et al. (2005) Am J Dermatopathol 27:96]. The expression of both Kit and Kit-ligand is increased in lesional vs. nonlesional skin, suggesting that Kit and Kit-ligand play an important role in the mechanism of hyper-pigmentation in melasma [Kang et al. (2006) Br J Dermatol 154:1094]. Accordingly, interfering with Kit signaling using the compounds of the present invention is expected to improve the appearance in melasma.

Lentigo Senilis

Lentigo senilis (LS) lesions, also called age spots, are pigmented spots characterized by increased melanin deposits localized in the basal and suprabasal layers of the epidermis, which are attributable to the stimulated proliferation and melanogenic activity of melanocytes. In LS lesional epidermis, there is an increased number of tyrosinase-positive melanocytes accompanied by an increased expression of tyrosinase mRNA in the skin [Kadono et al. (2001) J Invest Dermatol 116:571]. Clinical and histochemical features of LS are similar to UVB-induced hyperpigmentation in terms of a generally high localization to sun-exposed areas as well as the appearance of basal pigmentation and acanthosis [Hattori et al. (2004) J Invest Dermatol 122:1256]. Kit-ligand protein is overexpressed in the lesional epidermis, compared to the non-lesional skin, implicating Kit-ligand in the epidermal hyperpigmentation characteristic of LS lesions [Hattori et al. (2004) J Invest Dermatol 122:1256]. Accordingly, interfering with Kit signaling using the compounds of the present invention is expected to improve the appearance in LS.

In summary, Kit kinase is a highly validated pharmaceutical target for conditions involving hyperpigmentation or unwanted pigmentation of skin and hair. Accordingly, the present invention provides compositions for the treatment or prevention of such conditions, as well as for achieving desirable cosmetic effects, such as lightening or preventing darkening of the skin tone in the absence of pathology. Conditions of increased or undesirable pigmentation contemplated in the present invention include, but are not limited to, the following: Lentigo; Periorbital hyperpigmentation; Café-au-lait macules; Post-inflammatory hyperpigmentation; Becker's nevus, pigmented hair epidermal nevus; Nevus of Ota; Hori's nevus, acquired dermal melanocytosis; Melasma, chloasma, mask of pregnancy; Ephelides, freckles; Dyschromatosis symmetrica hereditaria, symmetrical dyschromatosis of the extremities; Acropigmentatio reticularis; PeuizJeghers syndrome; Pigmentation secondary to endocrinopathies; Mongolian spot, congenital dermal melanocytosis; Nevus of Ito, nevus fusco-caeruleus acromiodeltoides; Incontinentia pigmenti; Acanthosis nigricans; Riehl's melanosis; Drug-induced hyperpigmentation; Erythema dyschromicum perstans; and Nevi.

Mastocytosis

Mastocytosis or mast cell disease is a heterogeneous group of conditions characterized by increased numbers of mast cells in various organs, frequently the skin [Longley (1999) Cutis 64:281]. One form, urticaria pigmentosa, is characterized by multiple discrete hyperpigmented lesions. A number of studies suggested that abnormal Kit signaling could cause mastocytosis. These include a demonstration of increased levels of Kit-ligand (also referred to as mast-cell growth factor) in the skin of patients with cutaneous mastocytosis [Longley et al. (1993) N Engl J Med 328:1302], and identification of mutations resulting in constitutive activation of Kit receptor expressed in skin mast cells of patients [Longley et al. (1996) Nat Genet. 12:312, Longley et al. (2000) Hematol Oncol Clin North Am 14:697]. In summary, inhibition of Kit kinase presents a promising strategy for treatment of at least some sub-types of mastocytosis. See also U.S. Pat. No. 6,977,159 (Issued: Dec. 20, 2005) disclosing a method of inhibiting Kit-ligand/Kit signaling for the treatment of mastocytosis. Accordingly, the present invention provides compounds and compositions for the treatment of cutaneous mastocytosis sensitive to Kit inhibition via inhibition of Kit kinase activity.

The inventive compounds can be administered conjointly (e.g., simultaneously or sequentially, in one or different compositions, to one or different sites) with other treatments or compounds, wherein such conjoint administration can enhance the utility of the inventive compounds and compositions for treatment of Kit diseases, or for achieving cosmetically useful outcomes, e.g. involving reducing skin or hair pigmentation. Such combination treatments can include, for example, anti-inflammatory agents (e.g. glucocorticoids or steroids), skin lightening or anti-hyperpigmentation agents (e.g. retinoids, hydroquinone, glycolic acid, trichloroacetic acid, arbutin, or kojic acid), anti-fibrotic agents (e.g., pirfenidone, halofuginone, or tranilast), anti-pruritic agents (e.g., antihistamines such as diphenhydramine), sunscreens, aloe-emodin, and anti-infective agents such as antibiotics or antimycotics.

Pharmaceutical Compositions of the Invention and Routes of Administration

For administration to human and animal patients, the inventive compounds can be formulated in pharmaceutical compositions in combination with one or more pharmaceutically acceptable carriers and/or excipients, such any conventional solvents and diluents (e.g., water, physiological solution, glycerol, ethanol, and the like) as well as combinations thereof, buffers, wetting agents, antioxidants, stabilizers, conservants, coatings, colorants, fragrances and flavorants, disintegrants, emulgators, fillers, lubricants, permeation or penetration enhancers, absorption delaying agents, antibacterial and anti-fungal agents, as well as other well-known agents which enhance the shelf life or effectiveness of one or more of the active components of the composition. Examples of such useful substances can be found e.g. in Remington: the science and practice of pharmacy, Lippincott Williams & Wilkins 2005, and in Handbook of pharmaceutical excipients, Rowe R C, Sheskey P J, Quinn M E, eds., Pharmaceutical Press 2009; indeed, the use of such substances is integral to the practice of the art, and is also extensively discussed in other references provided herein. Except insofar as any conventional media or agent is incompatible with the active ingredient, use thereof in the inventive compositions is contemplated.

The compositions of the present invention may be formulated for delivery via any route known in the art. Topical administration is a preferred route of administration. Topical compositions useful in the subject invention may be formulated by any means known in the art, e.g. as described in Topical and Transdermal Drug Delivery: Principles and Practice. Benson H A E, Watkinson A C, eds. Wiley 2011, and in Topical Drug Delivery Formulations. Osborne D W, Amann A H, eds. Marcel Dekker 1990. For example, the inventive compounds may be formulated as an ointment, by suspending or dissolving them in a mixture with one or more of the following: mineral oil, petrolatum, propylene glycol, emulsifying wax, polysorbate, cetearyl alcohol, benzyl alcohol, and water; as emulsions comprising an emulsifier(s); or as a gel, e.g. a water-based gel using gelling agents such as natural gums, acrylic acid and acrylate polymers and copolymers, and cellulose derivatives (e.g., hydroxymethyl cellulose and hydroxypropyl cellulose). The topical compositions may be made into a wide variety of product types that include solutions, lotions, creams, gels, sticks, sprays, ointments, pastes, foams, powders, mousses, patches, hydrogels, and films. The skilled artisan will take into account the desirability of matching the properties of the formulation with the intended use such that, e.g. in topical formulations for use on skin, the proper layer of the skin be preferentially targeted; for example, to target melanocytes in the epidermal layer of the skin for a formulation intended to modify skin pigmentation, one useful approach is to select the formulation that preferentially deposits or retains the active components of the formulation, such as inventive compounds, in the proximity of the epidermal layer.

Pharmaceutical compositions of this invention may be formulated to modify and control the distribution of the substances (e.g. the inventive compounds) present in a composition, upon administration to the subject; such controlled release formulations are well known and widely practiced in the art; see e.g. Wise D L. Handbook of pharmaceutical controlled release technology. New York: Marcel Dekker 2000, and Li X P, Jasti B R. Design of controlled release drug delivery systems. New York: McGraw-Hill 2006.

Pharmaceutical compositions of this invention include cosmetic compositions. Such cosmetic compositions are preferably topical and may comprise, optionally in addition to other substances and components generally useful in topical formulations as disclosed herein, also one or more cosmetically useful substance or component such as fragrances, antioxidants; amino acids, peptides, plant or other extracts, vitamins, coloration agents, including coloration blocking agents, sunscreens, thickeners or gelling agents employed to confer pleasing tactile properties on the formulation, and the like. Such cosmetically useful substances and components are well known in the art; selected examples, as well as guidance useful to one skilled in the art in preparing cosmetic compositions, may be found in, for instance, Flick EW Cosmetic and toiletry formulations. Park Ridge, N.J., U.S.A.: Noyes Publications 1989, Draelos Z K, Thaman L A Cosmetic formulation of skin care products. New York: Taylor & Francis 2006, Barel A O, Paye M, Maibach H I. Handbook of cosmetic science and technology. New York: Informa Healthcare 2009, and Rosen M R Delivery system handbook for personal care and cosmetic products: technology, applications, and formulations. Norwich, N.Y.: William Andrew Pub 2005.

Compound Administration and Effective Amounts

With the aid of present disclosure, skilled artisans should be able to derive suitable dosages and schedules of administration for any of a number of suitable compositions that contain the inventive compounds. As disclosed herein, the quantities of the compounds appropriate for administration to the subject are those established to be generally safe and also therapeutically or cosmetically effective. A compound may be administered at a dose, for instance, from about 0.02 mg/kg to about 200 mg/kg locally, or in topical application, at a dose, commensurate with the area being treated, of a composition containing about 0.01% to 20%, e.g., 0.1% to 10%, e.g., 1% to 5% of the inventive compound by weight.

Pharmaceutical compositions within the scope of the present invention include compositions where the inventive active ingredient is contained in an amount effective for inhibiting Kit kinase activity in a cell. The efficacy of the inventive compounds and compositions can be determined using the in vitro and in vivo assays. Useful in vitro assays include assays for monitoring inhibition of Kit kinase, such as (i) radiometric-based filtration binding assays (e.g., Millipore's KinaseProfiler assay); (ii) scintillation proximity assays (e.g., FlashPlate assay from ProQinase); (iii) enzyme-linked immunosorbent assays (ELISA) (e.g., ProQinase GmbH (Freiburg, Germany) substrate specific sandwich enzyme-linked immunosorbent assay); and (iv) luminescence assays (e.g., Promega's Kinase-Glo Luminescent Kinase Assay); a good introduction is provided by Ma et al. (2008) Expert Opin Drug Discov 3:607.

Therapeutically effective dosages according to the present invention can be determined stepwise by combinations of approaches such as (i) characterization of effective doses of the compound in in vitro assays using Kit kinase activity as a readout followed by (ii) characterization in cell cultures using Kit kinase activity and/or decrease in melanin production, using e.g. MelanoDerm assay, followed by (iii) characterization in animal studies using, e.g., the amount of melanin in UV irradiated specimens as a readout, followed by (iv) characterization in human trials using objective colorimetric assessment of the skin color of pigmented lesions as a readout. The therapeutically effective dosage may be determined in the context of a particular route of administration and dosing schedule. In a preferred embodiment, the route of administration is topical. In a further preferred embodiment, therapeutically effective dosage is determined by clinical experimentation using previously tested dosage of FPL-62064, 2% to 8% by weight, in a topical formulation ([Blackham et al. (1990) Agents Actions 30:432] and Example 3), as a starting point. In one aspect, the dosing schedule is twice a day (bid), in the morning and evening. In a preferred embodiment, the dosing amount and schedule are adjusted by a health professional observing the subject, or by the subject. In one aspect, the dosing is adjusted once the desired therapeutic effect is achieved, such that the new dosing, e.g. reduced dosing, is sufficient to maintain the desired effect.

Cosmetically effective dosages according to the present invention, e.g. for a topical cosmetic formulation intended to elicit lightening of the skin tone, can be determined stepwise by combinations of approaches such as, e.g., (i) characterization of effective doses of the compound in in vitro assays using Kit kinase activity as a readout followed by (ii) characterization in cell cultures using Kit kinase activity and/or decrease in melanin production, using, e.g., MelanoDerm assay, followed by (iii) characterization in animal studies using, e.g., the amount of melanin in UV irradiated specimens as a readout, followed by (iv) characterization in human trials using as a readout objective colorimetric assessment of the skin color, or a subjective assessment of the effect, e.g. by the subject. The cosmetically effective dosage may be determined in the context of a particular route of administration and dosing schedule. In a preferred embodiment, the route of administration is topical. In a further preferred embodiment, cosmetically effective dosage is determined by clinical experimentation using previously tested dosage of FPL-62064, 2% to 8% by weight, in a topical formulation ([Blackham et al. (1990) Agents Actions 30:432] and Example 3), as a starting point. In one aspect, the dosing schedule is twice a day (bid), in the morning and evening. In a preferred embodiment, the dosing amount and schedule are adjusted by the subject. In one aspect, the dosing is adjusted once the desired cosmetic effect is achieved, such that the new dosing, e.g. reduced dosing, is sufficient to maintain the desired effect.

Following methodologies that are well-established in the art, effective doses and toxicity of the inventive compounds and compositions, which performed well in in vitro tests, can be determined in studies using small animal models (e.g., mice, rats or guinea pigs) in which they have been found to be therapeutically effective and in which these drugs can be administered by the same route proposed for the human trials. For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial. Safety testing and the selection of the appropriate compositions and dosing is discussed e.g. in Drug Discovery and Evaluation: Safety and Pharmacokinetic Assays. Vogel H G, Hock F J, Maas J, Mayer D, eds. Springer 2006, in Preclinical development handbook: Toxicology. Gad S. C., ed. Hoboken, N.J.: Wiley-Interscience 2008; and particularly with regards to topical drugs and cosmetics, in Principles and practice of skin toxicology. Chilcott R P, Price S, eds. Hoboken, N.J.: John Wiley & Sons 2008, Marzulli and Maibach's dermatotoxicology. Maibach H I, Wilhelm K-P, Zhai H, eds. Boca Raton: CRC Press 2008, and in Dermatologic, cosmeceutic, and cosmetic development. Walters K A, Roberts M S, eds. New York: Informa Healthcare 2008.

The suitable therapeutically or cosmetically effective amount of a compound or composition of this invention may be determined experimentally, taking into consideration such factors as the exact mode of administration, the form in which the compound is administered, the indication being addressed, the subject involved (e.g., body weight, health, age, sex, etc.), and the preference and experience of the physician or veterinarian in charge, or for cosmetic applications, the preference of the human subject.

In practicing the invention, the formulation and dose for therapeutic administration of the inventive compounds will depend on the severity of the condition being treated, whether other drugs are being administered, the weight, age, and sex of the subject, and other criteria. In topical administration, the amount of the inventive composition applied will naturally depend on the extent of the site being treated. The skilled medical practitioner or cosmetologist will be able to select the appropriate formulation, amount, and dose in view of these criteria and based on the results of published clinical trials. The dosage and administration regimen can be further adjusted for a particular subject by monitoring the desired effects, e.g., skin pigmentation.

The compositions used in the methods of the present invention may additionally comprise further substances, including the substances that may be capable of contributing to the intended effect of the administration of such a composition. For instance, the compositions of the present invention may comprise other agents known to lighten the skin. In certain embodiments, the effect of having an inventive compound, as well as another active ingredient, may be such that the amount of each or some of the active ingredients may be significantly reduced, e.g., a synergistic effect (compared to the amount of such ingredient(s) needed to produce the same effect when used independently), while keeping the effect the same, or alternatively, that the effect will be significantly enhanced with the same amounts of the active ingredients; the above phenomenon may be additive, or super-additive, or synergistic.

A physical treatment modality is used herein to refer to a treatment modality working through the application of concentrated energy emitted by a device, or through application of mechanical force or means, including, e.g., surgery, such as cosmetic surgery, acupuncture, microdermabrasion, Intense Pulsed Light (IPL), Laser, Radiofrequency therapy, and Ultrasound treatment modalities. Treatment with physical treatment modalities, such as surgery, IPL, or Laser, are known in the art to occasionally result in the development of undesirable pigmentation. Accordingly, the methods, compounds and compositions described in the present disclosure are useful in conjunction with physical treatment modalities to treat, inhibit, or prevent such undesirable pigmentation.

Intense Pulsed Light (IPL). Therapeutic IPL devices are based on the principle of selective photothermolysis, wherein a chromophore in the tissue is excited with a light source, causing local hyperthermia and destroying undesirable tissue. IPL sources are widely used in medicine for various cosmetic problems, including vascular lesions, irregular pigmentation, telangiectasias, hypertrichosis, and rhytides. IPL differs from laser in that non-coherent (not a single wave length) light is used. IPL treatment is discussed in Gold (2007) Facial Plast Surg Clin North Am 15:145 and Ciocon et al. (2009) Facial Plast Surg 25:290. Laser. Coherent (single wave-length), low-divergence light sources are referred to as lasers. A variety of laser devices is available, including pulsed dye laser (PDL), quality-switched (Q-switched) lasers, e.g. Nd:YAG (neodymium-doped yttrium aluminum garnet) laser, and ablative laser systems, e.g. $CO_2$ lasers, and they are applied to numerous uses in medicine, in particular in dermatology, and in cosmetic treatments [Applied Laser Medicine. Breuer H, Krasner N, eds. Springer 2003]. Selected applications in dermatology include elimination of superficial vascular abnormalities, tattoo and hair removal, and mitigation of pigmented lesions [Watanabe (2008) Arch Dermatol Res 300 Suppl 1:S21, Jasim et al. (2007) J Am Acad Dermatol 57:677]. Radiofrequency therapy. Radiofrequency technology uses electrical current instead of light energy to create thermal damage in the deep dermis and subcutaneous tissue, beyond the reach of therapeutic laser light sources. Radiofrequency technology has been used e.g. in the treatment of acne and in photorejuvenation. Ultrasound. The term "ultrasound" refers to high-frequency acoustic waves up to about 100 MHz and beyond, capable of inducing controlled hyperthermia (elevated temperature is induced in a region of the body for therapeutic purposes) or cavitation in tissue. By heating with ultrasound, it is possible to apply stress to, and even to ablate, undesirable or diseased tissue without significant damage to surrounding healthy tissue. The uses of ultrasound in medicine are described in Physical principles of medical ultrasonics. Hill C R, ed. John Wiley & Sons 2004.

EXAMPLES

The present inventions are further described by way of the following particular examples. However, the use of such examples is illustrative only and is not intended to limit the scope or meaning of the inventions or of any exemplified term. Nor are the inventions limited to any particular preferred implementations or embodiment(s) described herein. Indeed, many modifications and variations of the inventions will be apparent to those skilled in the art upon reading this specification, and such "equivalents" can be made without departing from the inventions in spirit or scope. The inventions are therefore limited only by the terms of the appended claims, along with the full scope of equivalents to which the claims are entitled.

Example 1

Figure 1:
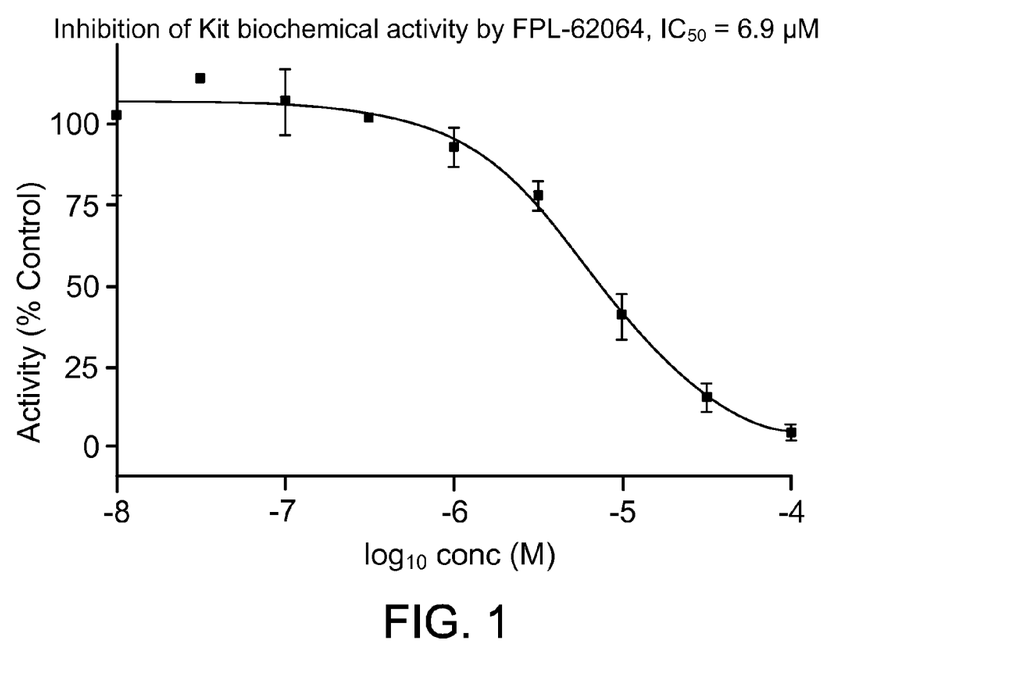
FIG. 1 is a graph showing inhibition of Kit kinase biochemical activity by FPL-62064 as determined in a Millipore KinaseProfiler radiometric-based filtration binding assay. The figure reports % residual activity of the kinase.

Biochemical Study of Efficacy of FPL-62064 Inhibition of Kit Receptor Tyrosine Kinase To characterize the inhibitory activity of FPL-62064 against Kit kinase, the drug was tested using Millipore KinaseProfiler radiometric-based filtration binding assay (EMD Millipore Corporation, Billerica, Mass.). In a final reaction volume of 25 µL, Kit (human) (5-10 mU) was incubated with 8 mM MOPS pH 7.0, 0.2 mM EDTA, 10 mM $MnCl_2$, 0.1 mg/mL poly(Glu, Tyr) 4:1, 10 mM MgAcetate and 10 µM [$\gamma^{33}$P-ATP] (specific activity approx. 500 cpm/pmol). The reaction was initiated by the addition of the MgATP mix. After incubation for 40 minutes at room temperature, the reaction was stopped by the addition of 5 µL of a 3% phosphoric acid solution. 10 µL of the reaction was then spotted onto a Filtermat A and washed three times for 5 minutes in 75 mM phosphoric acid and once in methanol prior to drying and scintillation counting. As shown in FIG. 1, FPL-62064 efficiently inhibits Kit kinase with $IC_{50}$ of 6.9 µM (2 µg/ml).

Example 2

Figure 2:
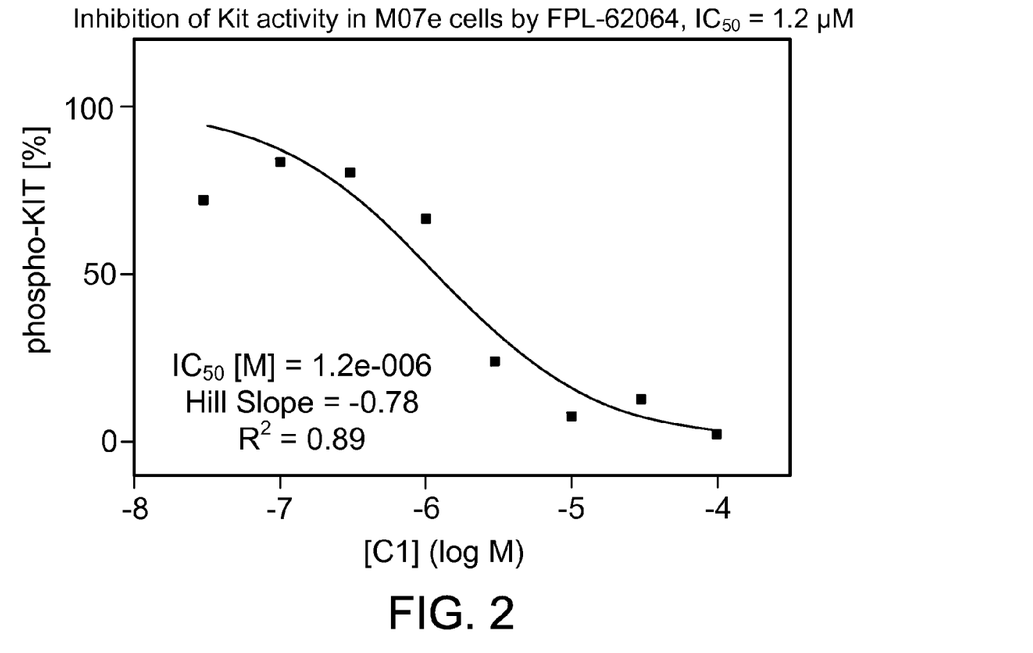
FIG. 2 is a graph that reports inhibition of Kit kinase autophosphorylation in M07e cells by FPL-62064 as determined by a ProQinase GmbH (Freiburg, Germany) substrate specific sandwich enzyme-linked immunosorbent assay (ELISA).

Inhibitory Impact of FPL-62064 on the Kinase Activity of Kit Receptor Tyrosine Kinase in Cells To characterize inhibitory impact of FPL-62064 on the cellular kinase activity of Kit, the drug was tested at ProQinase GmbH (Freiburg, Germany), as follows. The human acute megakaryoblastic leukemia cell line M07e expressing endogenously a high level of wild-type Kit was used in the cellular Kit phosphorylation assay. Stimulation of these cells with human Kit ligand results in receptor tyrosine autophosphorylation. M07e cells were plated in RPMI supplemented with 20% FCS and 10 ng/ml GM-CSF in multiwell cell culture plates. After serum- and growth factor-starvation overnight, cells were incubated with test compounds in serum-free medium. Pre-diluted test samples were added 1:100 to the cell culture medium resulting in a final DMSO concentration of 1%. After 90 minute incubation at 37° C., cells were stimulated with 100 ng/ml Kit ligand for 3 minutes. Cells treated with staurosporine were defined as Low control, and cells treated with solvent alone were defined as High control. Test sample-treated cells, as well as High and Low control, were stimulated in identical manner. Quantification of substrate phosphorylation was assessed in 96 well plates via sandwich ELISA using a substrate specific capture antibody and an anti-phosphotyrosine detection antibody. Raw data were converted into percent substrate phosphorylation relative to High control, set to 100%. $IC_{50}$ values were determined using GraphPad Prism 5.01 software with constrain of bottom to 0 and top to 100 using a nonlinear regression curve fit with variable Hill slope. The equation is a four-parameter logistic equation. Data quality was judged by comparing the $IC_{50}$ value of the reference compound (sunitinib) with the reference value obtained with this compound in earlier test runs. The $IC_{50}$ value obtained for sunitinib during the current project ($IC_{50}$=1.3 nM) reproduced the expected value of 0.8 nM (average $IC_{50}$ calculated over three runs previously performed at ProQinase). $IC_{50}$ curve describing FPL-62064 inhibition of Kit mediated autophosphorylation is shown in FIG. 2. The data shows that FPL-62064 efficiently inhibits Kit kinase activity in cells with $IC_{50}$ of 1.2 µM (0.3 µg/ml).

Subjects.

All subjects were recruited from Guangzhou area (China) community and were screened by the investigators. 6 individuals (1 male and 5 females; average age 26 years old, range 22-34 years old) were enrolled and entered the study. Subjects 2, 3, and 4 entered the study on day 1; subjects 8, 9, and 10 entered the study on day 4. All 6 subjects completed the study.

Test Materials.

The following test formulations were prepared and pH of each formulation was measured, as shown below. All the materials were pharmaceutical, analytical, or HPLC grade.

| Composition (g/100 g) | Formulation A 2% Gel | Formulation B 4% Gel | Formulation C 8% Gel | Formulation D Vehicle Control |
|---|---|---|---|---|
| FPL-62064 | 2 | 4 | 8 | 0 |
| Ultrez 10 NF | 0.4 | 0.4 | 0.4 | 0.4 |
| Propylene glycol | 2 | 2 | 2 | 2 |
| Ethanol | 56 | 56 | 56 | 56 |
| Triethanolamine | 0.4 | 0.4 | 0.4 | 0.4 |
| Water | 39.2 | 37.2 | 33.2 | 41.2 |
| pH | 7.64 | 7.41 | 7.58 | 7.68 |

Example 3

Safety and Efficacy of Skin Lightening Agent FPL-62064 on Darker Human Skin: a Single-Blind Pilot Clinical Study The objective of this pilot study was to evaluate whether FPL-62064 possesses the lightening effect in comparison with its vehicle, using objective instrumental data and visual scoring. The study protocol and informed consent form were reviewed and approved by the Guangzhou Institutional Review Board (Guangzhou, China) prior to the initiation of the study.

Inclusion Criteria.

A subject was eligible for inclusion in this study if all the following criteria were met: (1) The subject was Chinese with a darker skin tone; (2) The subject (male or female) was at least 18 years old and was healthy as judged by medical history and investigator's assessment of current health; (3) The subject had no obvious skin disease; (4) The subject was willing to refrain from using any topical products on his (her) back during the study; (5) The subject was willing to refrain from sun exposure during test period; (6) The subject understood their responsibility and role in the study and agreed to appear for all scheduled treatments, return to the clinic for the follow-up visits, and comply with all study requirements; (7) The subject had signed the Institutional Review Board (IRB)-approved informed consent form.

Exclusion Criteria.

A subject was not eligible for this study if any of the following criteria applied: (1) Pregnant or nursing women; (2) Significant history or current evidence of any medical, psychological or other disorder that, in the investigator's opinion, would preclude enrollment into the study; (3) Use of any dermatological drug therapy (including topical corticosteroids) or other skin care products on the backs during the study; (4) Skin sensitivity to ethanol, as determined using the "ethanol patch test": a patch of absorbent material containing 70% ethanol was applied to the skin for 15 minutes, and the subject was observed for 1 hr. Emergence of transient erythema at the site of patch application (typically seen within 20-30 min) indicated ethanol sensitivity.

Formulation E contained active ingredients identical to those of the FDA-approved branded pharmaceutical product Tri-Luna (Galderma): fluocinolone acetonide 0.01%, hydroquinone 4%, tretinoin 0.05%, in a commercial hydrophilic cream base.

Application.

Lower back of each subject was used as the test area. Five identically sized application sites (square 3 cm by 3 cm) were marked on the skin of each subject and labeled A through E. 0.1 gram of each material, as measured by extrusion from a syringe, was applied on the appropriate site, using a gloved finger, by a trained technician, guided by markings on the skin and the application site diagram. The application was carried out in an accredited outpatient facility twice daily (morning and afternoon/evening), 6 days per week (with no treatments on Sunday). The procedure was continued in the same manner for the duration of the study. Subjects 2, 3 and 4 entered the study on day 1 (Friday) and each received 48 treatments (no subject missed any of the treatments). Subjects 8, 9, and 10 entered the study on day 4 (Monday) and each received 44 treatments. No subject missed any of the treatments.

Assessment and Measurement Schedule.

Visual Scoring Scale: 0=no change; 1=barely visibly lightening; 2=clear lightening; 3=moderate lightening; 4=marked lightening. Visual scoring was conducted by a licensed clinical dermatologist.

Instrument Measurements:

L value (brightness) reading was taken in duplicate with the spectrophotometer CM-2600d (Konica Minolta, Osaka, Japan). The melanin (M) index reading was taken in duplicate with a Mexameter® MX18 (Courage & Khazaka, Cologne, Germany). On day 1 of the study for subjects 2, 3 and 4, and on day 4 of the study for subjects 8, 9, and 10, prior to any treatment, "baseline" visual assessment and instrumental measurements were carried out. For all subjects, visual assessment and instrumental measurements were carried out on the 8th, 15th, and 22nd day of the study, prior to the morning treatment. For all subjects, the final visual assessment and instrumental measurements were carried out on day 29.

Statistical Analysis.

Statistical analysis was performed using the computer program SigmaStat 11 (Systat Software Inc., Chicago, Ill., USA)

on a Microsoft Windows computer. For all data (Visual Scoring (VS), L value (brightness) (L), and Melanin Index (M)), the baseline readings were subtracted prior to analysis. For each of the L and M values, the analysis was performed using the average of the two readings. For non-parametric data (visual score), data were analyzed utilizing the Friedman Repeated Measures Analysis of Variance on Ranks combined with Dunnett's Method for the Multiple Comparisons versus Control Group (Formulation D, vehicle). Parametric data (L and M values) were analyzed with the One Way Repeated Measures Analysis of Variance (ANOVA) combined with Dunnett's Method for the Multiple Comparisons versus Control Group (Formulation D, vehicle). Statistical significance was accepted at p<0.05.

Safety and Adverse Events.

FPL-62064: No edema, erythema, scaling, or any other evidence of sensitivity or irritation were observed for any of the formulations containing FPL-62064 (Formulations A, B, and C) at any time point during the study. Positive Control: Erythema, scaling, papules, itching, and/or areas of hyperpigmentation were observed for subjects 2, 3, 4, 8, and 10. In all cases, the condition of the sites treated with Formulation E improved upon termination of the treatment. Vehicle: No edema, erythema, scaling, or any other evidence of sensitivity or irritation were observed for the vehicle control (Formulation D) at any time point during the study.

Skin Lightening Data.

The visual score (VS), and the difference from baseline for each of the L value (L) and melanin index (M), averaged over all subjects, day 8; 15; 22; and day 29 are given below. The baseline was day 1 for subjects 2, 3 and 4; and day 4 for subjects 8, 9, and 10. The final measurements (on day 29) for Formulation E, the positive control, were conducted attempting to avoid regions of visible irritation, scaling, or hyperpigmentation; nonetheless, the above factors confound the interpretation of the efficacy of the positive control.

Summary.

(1) FPL-62064 at all concentrations used (2%, 4%, and 8%) was well tolerated: no adverse events were observed in any of the subjects throughout the study. (2) FPL-62064 showed activity as a skin lightening agent: (a) at the end of the study, for the Formulation C (8% FPL-62064), skin lightening was statistically significant according to all three metrics employed: visual score, L value (brightness), and melanin M index; (b) at the end of the study, for the Formulation B (4% FPL-62064), statistically significant change was observed in L value (brightness) and melanin M index; (c) at the end of the study, for the Formulation A (2% FPL-62064), statistically significant change was observed in melanin M index; (d) at the end of the study, visual score 2, "clear lightening", was reported for the Formulation C (8% FPL-62064) in 4 out of 6 subjects; (e) at the end of the study, the average decrease in melanin M index from baseline was 19.7 units for Formulation A (2% FPL-62064), 24.6 units for Formulation B (4% FPL-62064), and 26.3 units for Formulation C (8% FPL-62064); (f) measured decrease in melanin M index appears to occur in a concentration-dependent manner.

Other Embodiments

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

|  | Formulation A | | | Formulation B | | | Formulation C | | | Formulation D | | | Formulation E | | |
| --- | --- | --- | --- | --- | --- | --- | --- | --- | --- | --- | --- | --- | --- | --- | --- |
|  | VS | L | M | VS | L | M | VS | L | M | VS | L | M | VS | L | M |
| Day 8 | 0.5 | 0.2 | −5.6 | 0.5 | 0.5 | −6.3 | 0.3 | 0.2 | −9.3 | 0.3 | 0.3 | −2.4 | 0.5 | 0.8 | −11.3 |
| Day 15 | 1.0 | 0.3 | −6.7 | 1.0 | 0.7 | −12.8 | 1.0 | 0.6 | −16.8 | 1.0 | 0.9 | −4.9 | 1.0 | 0.5 | −23.8 |
| Day 22 | 1.0 | 0.6 | −11.9 | 1.0 | 1.3 | −17.5 | 1.0 | 0.9 | −20.2 | 1.0 | 0.4 | −4.5 | 1.2 | 0.1 | −11.3 |
| Day 29 | 1.0 | 1.0 | −19.7 | 1.2 | 1.6 | −24.6 | 1.7 | 1.3 | −26.3 | 1.0 | 0.2 | −4.4 | 1.0 | 0.3 | −30.0 |

Skin Lightening Data Analysis.

Figure 3:
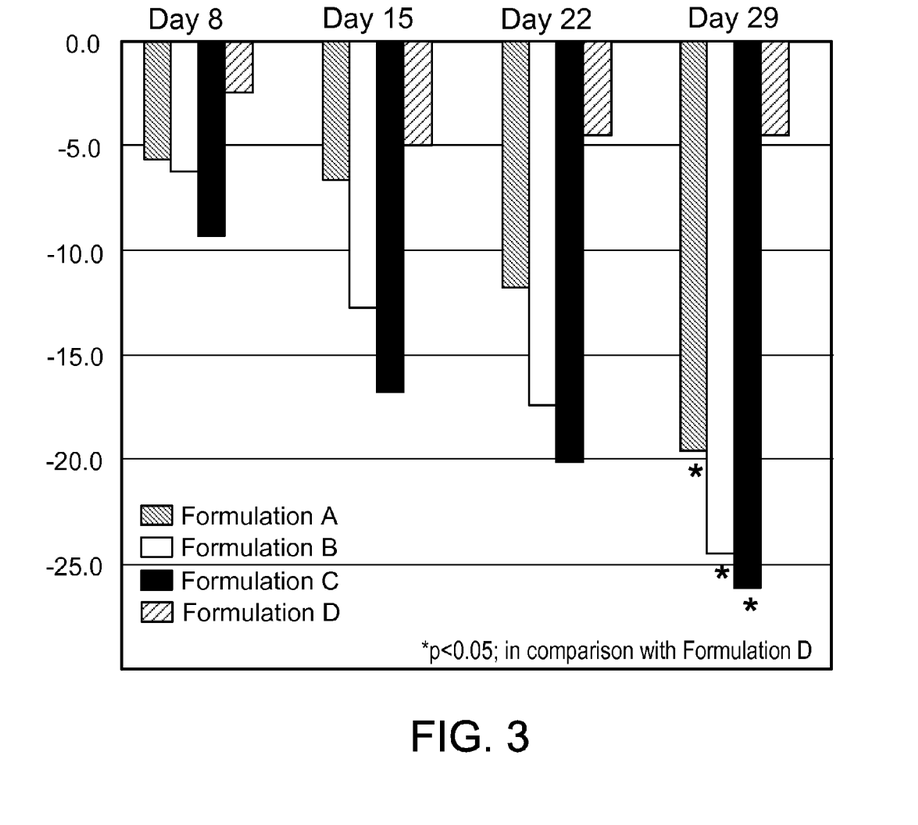
FIG. 3 is a bar graph that reports the reduction of melanin index in skin of darker skin subjects during a clinical study with different formulations of FPL-62064. Formulation A: 2% FPL-62064; Formulation B: 4% FPL-62064; Formulation C: 8% FPL-62064; Formulation D: Vehicle.

Visual Score (VS): On day 29, the site treated with the Formulation C (FPL-62064 8%) demonstrated a significant (p<0.05) increase in visual lightness score in comparison with the control site (Formulation D, vehicle). Visual score 2, "clear lightening" was reported for the Formulation C (8% FPL-62064) in 4 out of 6 subjects. L value (brightness): On day 29, the sites treated with Formulations B and C (FPL-62064 4% and 8%, respectively) showed significant (p<0.05) increase in L value (brightness) from baseline—consistent with skin lightening—vs. the control site (Formulation D, vehicle). Melanin Index: On day 29 of the study, each of the sites treated with Formulations A, B and C (FPL-62064 2%, 4%, and 8%, respectively), and Formulation E (positive control) demonstrated significant (p<0.05) reduction of the melanin index (M) from baseline, consistent with skin lightening, compared to the control site (Formulation D, vehicle). Change in the melanin index over the course of the study is shown in FIG. 3.

All references cited herein, including all patents, published patent applications, and published scientific articles, are incorporated by reference in their entireties for all purposes.

What is claimed is:

1. A method for reducing, or inhibiting the increase, of skin or hair pigmentation, or for treating a skin pigmentation condition, comprising administering to a subject in need thereof an effective amount of N-(4-methoxyphenyl)-1-phenyl-1H-pyrazol-3-amine (FPL-62064) or a pharmaceutically acceptable salt, ester, or prodrug thereof.

2. The method according to claim 1 for treating a skin pigmentation condition.

3. The method according to claim 2, where the skin pigmentation condition is selected from the group consisting of melasma, freckles, lentigines, cafe-au-lait macules, acanthosis nigricans, nevi, periorbital hyperpigmentation, post-inflammatory hyperpigmentation, and drug-induced hyperpigmentation.

* * * * *